(12) United States Patent
Johnson et al.

(10) Patent No.: US 8,536,182 B2
(45) Date of Patent: Sep. 17, 2013

(54) BENZYLPIPERAZINE DERIVATIVES AND THEIR MEDICAL USE

(75) Inventors: Christopher Norbert Johnson, Harlow (GB); David Timothy Macpherson, Harlow (GB); Steven James Stanway, Harlow (GB); Geoffrey Stemp, Harlow (GB); Mervyn Thompson, Harlow (GB); Susan Marie Westaway, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 810 days.

(21) Appl. No.: 11/996,650

(22) PCT Filed: Jul. 24, 2006

(86) PCT No.: PCT/EP2006/007390
§ 371 (c)(1),
(2), (4) Date: Jul. 30, 2008

(87) PCT Pub. No.: WO2007/012479
PCT Pub. Date: Feb. 1, 2007

(65) Prior Publication Data
US 2009/0054456 A1    Feb. 26, 2009

(30) Foreign Application Priority Data

Jul. 26, 2005    (GB) .................................. 0515381.2
Jun. 9, 2006     (GB) .................................. 0611469.8

(51) Int. Cl.
| | | |
|---|---|---|
| A61K 31/497 | (2006.01) | |
| A61K 31/44 | (2006.01) | |
| C07D 401/00 | (2006.01) | |
| C07D 405/00 | (2006.01) | |
| C07D 409/00 | (2006.01) | |
| C07D 411/00 | (2006.01) | |
| C07D 413/00 | (2006.01) | |
| C07D 417/00 | (2006.01) | |
| C07D 419/00 | (2006.01) | |
| C07D 421/00 | (2006.01) | |

(52) U.S. Cl.
USPC ...... 514/253.13; 514/326; 514/357; 514/866; 514/872; 544/380; 546/210

(58) Field of Classification Search
USPC ................. 514/253.13, 356, 357, 866, 872; 544/360; 546/210
See application file for complete search history.

(56) References Cited

U.S. PATENT DOCUMENTS

| | | |
|---|---|---|
| 5,385,912 A | 1/1995 | Neuenschwander et al. |
| 5,494,918 A | 2/1996 | Neuenschwander et al. |
| 5,593,994 A | 1/1997 | Batt et al. |
| 5,912,235 A | 6/1999 | Hoeltje et al. |
| 5,932,586 A | 8/1999 | Batt et al. |
| 5,965,578 A | 10/1999 | Graham et al. |
| 5,972,939 A | 10/1999 | Chen et al. |
| 6,100,239 A | 8/2000 | Ataka et al. |
| 6,165,985 A | 12/2000 | Jasserand et al. |
| 6,200,978 B1 | 3/2001 | Maw et al. |
| 6,384,031 B2 | 5/2002 | Chen et al. |
| 6,392,040 B2 | 5/2002 | Chen et al. |
| 6,423,714 B2 | 7/2002 | Chen et al. |
| 6,426,346 B1 | 7/2002 | Pruitt et al. |
| 6,624,165 B2 | 9/2003 | Chen et al. |
| 6,667,309 B2 | 12/2003 | Chen et al. |
| 6,977,264 B2 | 12/2005 | Fotsch et al. |
| 7,223,788 B2 | 5/2007 | Schwink et al. |
| 7,262,195 B2 | 8/2007 | Li et al. ..................... 514/252.06 |
| 7,700,599 B2 | 4/2010 | Thompson et al. ....... 514/253.12 |
| 7,767,692 B2 | 8/2010 | Jasserand et al. ............. 514/315 |
| 2002/0010184 A1 | 1/2002 | Dinsmore et al. |
| 2002/0052380 A1 | 5/2002 | Dinsmore et al. |
| 2003/0203922 A1 | 10/2003 | Patel et al. ................ 514/266.21 |
| 2004/0152732 A1 | 8/2004 | Jasserand et al. ............ 514/317 |
| 2005/0065156 A1 | 3/2005 | Li et al. ......................... 514/248 |
| 2005/0080116 A1 | 4/2005 | Li et al. ......................... 514/364 |

(Continued)

FOREIGN PATENT DOCUMENTS

| | | |
|---|---|---|
| JP | 09249620 | 9/1997 |
| WO | WO 94/10185 A1 | 5/1994 |

(Continued)

OTHER PUBLICATIONS

Li, et al. Journal of Medicinal Chemistry, 47(7):1704-1708, Mar. 2, 2004.

(Continued)

*Primary Examiner* — Paul Zarek

(74) *Attorney, Agent, or Firm* — Kathryn A. Lutomski; John Lemanowicz

(57) ABSTRACT

The present invention relates to novel benzylpiperazine derivatives such as compounds of formula (I), which have activity as agonists of the GPR38 receptor and the use of such compounds or pharmaceutical compositions thereof in the treatment of gastrointestinal disorders.

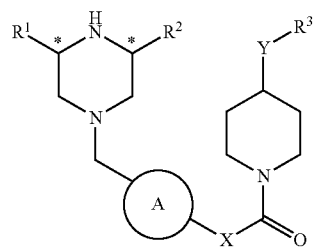

16 Claims, No Drawings

(56) References Cited

U.S. PATENT DOCUMENTS

| | | |
|---|---|---|
| 2005/0272722 A1 | 12/2005 | Lansbury et al. |
| 2005/0277629 A1 | 12/2005 | Lansbury et al. |
| 2005/0288298 A1 | 12/2005 | Lansbury et al. |
| 2006/0106060 A1 | 5/2006 | Lansbury et al. |
| 2007/0225292 A1 | 9/2007 | Amin et al. ............. 514/252.1 |
| 2007/0293539 A1 | 12/2007 | Lansbury et al. |
| 2008/0027065 A1 | 1/2008 | Mitchell et al. ........ 514/252.11 |
| 2008/0306083 A1 | 12/2008 | MacDonald et al. ..... 514/253.1 |
| 2008/0312209 A1 | 12/2008 | MacDonald et al. .... 514/210.18 |
| 2009/0131453 A1 | 5/2009 | Seal et al. ............. 514/255.01 |
| 2009/0192160 A1 | 7/2009 | Mitchell et al. .......... 514/235.8 |
| 2010/0256364 A1 | 10/2010 | Mitchell et al. .............. 544/121 |

FOREIGN PATENT DOCUMENTS

| | | |
|---|---|---|
| WO | WO 01/85694 A | 11/2001 |
| WO | WO 2005/063720 A1 | 7/2005 |
| WO | WO 2005/077345 A1 | 8/2005 |
| WO | WO 2005/077368 A2 | 8/2005 |
| WO | WO 2005/077373 A2 | 8/2005 |
| WO | WO 2007/07018 A1 | 1/2007 |
| WO | WO 2007/012479 * | 2/2007 |
| WO | WO 2007/065669 A1 | 6/2007 |
| WO | WO 2007/144400 A1 | 12/2007 |
| WO | WO 2008/000729 A1 | 1/2008 |
| WO | WO 2009/068552 A1 | 6/2009 |

OTHER PUBLICATIONS

Vu, et al. Journal of Medicinal Chemistry, 47(17):4291-4299, Jul. 13, 2004.

Le Bihan, et al. Journal of Medicinal Chemistry, 42(9):1587-1603, Apr. 14, 1999.

Hayallah, et al. Journal of Medicinal Chemistry, 45(7):1500-1510, Feb. 14, 2002.

*Chemical Abstracts Service*, Caplus, XP002452868, 2005:612264 (2005).

Filewrapper for U.S. Appl. No. 11/995,416, filed Jun. 9, 2008.
Filewrapper for U.S. Appl. No. 12/096,104, filed Jun. 4, 2008.
Filewrapper for U.S. Appl. No. 12/304,539, filed Dec. 12, 2008.
Filewrapper for U.S. Appl. No. 11/768,339, filed Jun. 26, 2007.
Filewrapper for U.S. Appl. No. 12/417,176, filed Apr. 2, 2009.
Filewrapper for U.S. Appl. No. 12/744,367, filed May 24, 2010.

* cited by examiner

BENZYLPIPERAZINE DERIVATIVES AND THEIR MEDICAL USE

This application is a 371 of International Application No. PCT/EP2006/007390, filed 24 July 2006, which claims the priority of GB Application Nos. 0611469.8, filed 9 Jun. 2006 and 0515381.2, filed 25 Jul. 2005, which are incorporated herein in their entireties.

The present invention relates to novel benzylpiperazine derivatives having pharmacological activity, processes for their preparation, pharmaceutical compositions containing them and their use in the treatment of various disorders.

GPR38 is a 7-transmembrane, G-protein coupled receptor, with high affinity for the peptide motilin [Feighner et al., Science 1999, 284, 2184], suggesting that endogenous motilin exerts all or most of its activity via this receptor.

Motilin is a 22 amino acid peptide found in large amounts within endocrine-like cells of the gastrointestinal tract, and especially in the duodenum-jejunum areas. During fasting, the peptide is known to be associated with the onset of Phase III migrating complex activity within the stomach [Boivin et al., Dig. Dis. Sci. 1992, 37, 1562], suggesting a role in the mechanisms of prokinetic activity. Motilin is also released from the gut during feeding, sham feeding, gastric distension or by oral or intravenous nutrient application [Christofides et al., Gut 1979, 20, 102; Bormans et al., Scand. J. Gastroenterol. 1987, 22, 781], suggesting additional roles for this peptide in the modulation of motility patterns during feeding.

In animals or in man, motilin has long been known to increase gastrointestinal motility, and promote gastric emptying and intestinal propulsion in an anal direction, during both fasting and fed conditions. This activity is thought to be primarily due to a facilitation of at least the cholinergic excitatory function of the gut [Van Assche et al., Eur. J. Pharmacol. 1997, 337, 267], perhaps also involving the activation of the vagus nerve [Mathis & Malbert, Am. J. Physiol. 1998, 274, G80]. In addition, higher concentrations of motilin directly evoke a small contraction of the muscle [Van Assche et al., Eur. J. Pharmacol. 1997, 337, 267].

The antibiotic erythromycin was shown to mimic the gastrointestinal activity of motilin, in addition to its previously-described antibiotic properties [see Peeters, in *Problems of the Gastrointestinal Tract in Anaesthesia* Ed., Herbert M K et al. Springer-Verlag, Berlin, Heidelberg 1999, pp 39-51]. More recently, erythromycin has been shown to activate the GPR38 receptor, confirming its ability to mimic the function of motilin [Carreras et al., Analyt. Biochem. 2002, 300, 146]. In addition, the availability of this non-peptide motilin receptor agonist has allowed at least some clinical studies to be undertaken in order to examine the clinical potential of motilin receptor agonists. These studies have consistently demonstrated an ability to increase gastric emptying in various conditions associated with gastroparesis, such as functional dyspepsia and diabetic gastroparesis. Further, erythromycin has been shown to increase lower esophageal sphincter pressure in man, which together with the increase in gastric emptying, suggests a role in the treatment of gastroesophageal reflux disorders (GERD). Finally, erythromycin has been used to promote intestinal propulsive activity, finding clinical utility in the treatment of pseudo-obstruction and in conditions with impaired colonic motility [Peeters, in *Problems of the Gastrointestinal Tract in Anaesthesia* Ed., Herbert M K et al. Springer-Verlag, Berlin, Heidelberg 1999, pp 39-51].

Consequently it is expected that agonists at the GPR38 receptor will mimic the activity of motilin and find clinical utility in the treatment of gastrointestinal disorders associated with hypomotility, especially the functional bowel disorders such as GERD, functional dyspepsia (FD) and irritable bowel syndrome (IBS). The compounds will also be useful for the treatment of other GI conditions where the cause is known and in which GI motility is reduced. Such conditions include constipation, caused by various diseases such as those associated with neuropathy, and/or by the administration of other drugs, intestinal pseudo-obstruction, paralytic ileus following surgery or some other manipulation, gastric stasis or hypomotility caused by various diseases such as diabetes and/or by the administration of other drugs. Interestingly, the ability of motilin or erythromycin to activate the vagus nerve, the association of this nerve with changes in feeding behaviour [e.g. Furness et al., Auton. Neurosci. 2001, 92, 28] and the chromosomal location of GPR38 [based on Ensembl: 13q21.1 (58.46-59.46 Mb)] within the markers (D13S257-13q14.11 to D13S258 at 13q21.33) of a locus associated with obesity [Feitosa et al, Am. J. Hum. Genet. 2002, 70, 72] also suggests that agonists active at the GPR38 receptor will, in addition to promoting gastrointestinal motility, facilitate eating behaviours in at least those patients in which some degree of appetite suppression or cachexia is present. Such activity indicates that agonists at this receptor will find clinical utility in the treatment of symptoms associated with—for example—the treatment of cancer or by the presence of the cancer itself.

In addition to the ability of motilin receptor agonists to promote gastrointestinal motility, the association of motilin gene polymorphism with Crohn's disease [Annese et al., Dig. Dis. Sci. 1998, 43, 715-710] and the changes in motilin receptor density during colitis [Depoortere et al., Neurogastroenterol. Motil. 2001, 13, 55] suggests a utility for agonists at the motilin receptor for the treatment of inflammatory bowel conditions in general.

Finally, GPR38 is also found in regions outside the gastrointestinal tract. These areas include the pituitary, adipose tissue, urinary bladder and certain areas of the brain. The former suggests clinical utility in the promotion of pituitary function, such as the release of growth hormone secretagogues, the presence within adipose tissue again suggests a role in the control of body weight, and the presence within the urinary bladder suggests a role for agonists at this receptor in the treatment of incontinence. The presence of GPR38 within the brain supports the gastrointestinal and feeding utilities already mentioned, but in addition, suggests an involvement of the receptor in a greater spectrum of vagal-hypothalamic functions.

WO9410185, EP838469, WO9823629, DE19805822, and U.S. Pat. No. 6,165,985 claim erythromycin derivatives targeting GPR38 for use in disorders relating to gastrointestinal motility. WO9921846, WO0185694, WO0168620, WO0168621, and WO0168622 disclose a series of small molecule antagonists of the GPR38 receptor. JP07138284 and EP807639 disclose peptide agonists. JP09249620, WO02092592, WO05027637, US2005065156 and Li et al., (2004, Journal of Medicinal Chemistry, 47(7) p 1704-1708) disclose series of small molecule agonists.

A structurally novel class of compounds has now been found which provides partial or full agonists of the GPR38 receptor.

The present invention therefore provides compounds of formula (I) or pharmaceutically acceptable salts or solvates thereof:

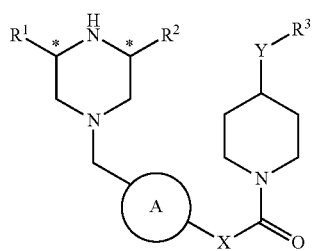

(I)

wherein:
A is phenyl or a 6-membered heteroaryl ring, optionally substituted with halogen, $C_{(1-4)}$alkyl or $C_{(1-4)}$alkoxy;
$R^1$ and $R^2$ are independently H or $C_{(1-4)}$ alkyl;
$R^3$ is optionally substituted phenyl or optionally substituted 5 or 6 membered heteroaryl;
X is $(CR^4R^5)_n$;
n is 1 or 2;
Y is NH, O or $CH_2$;
$R^4$ and $R^5$ are independently selected from hydrogen and $C_{(1-4)}$ alkyl.

When $R^3$ is substituted, it may have 1, 2 or 3 substituents, each independently selected from halogen, $C_{(1-4)}$alkyl, $C_{(1-4)}$ alkoxy, $C_{(3-7)}$cycloalkyl, hydroxy, trifluoromethoxy, trifluoromethyl, nitro, cyano, phenyl, $NH_2$, $NHR^8$, $NR^8R^9$, $NHCOR^8$, $NHSO_2R^8$, $C(O)CF_3$, $C(O)C_{(1-4)}$alkyl, $C(O)C_{(3-7)}$ cycloalkyl, $C(O)OC_{(1-4)}$alkyl, $C(O)OC_{(3-7)}$cycloalkyl, $OC(O)C_{(1-4)}$alkyl, $OC(O)C_{(3-7)}$cycloalkyl, $CONH_2$, $CONHR^8$, $CONR^8R^9$, $SOR^9$, $SO_2R^9$, $OSO_2R^9$, $OSO_2CF_3$, $SO_2NH_2$, $SO_2NHR^8$, $SO_2NR^8R^9$, where $R^8$ and $R^9$ may be the same or different and represent $C_{(1-4)}$ alkyl, phenyl optionally substituted with halogen or 5 or 6 membered heteroaryl optionally substituted with halogen.

The term "alkyl" as a group or part of a group e.g. alkoxy or hydroxyalkyl refers to a straight or branched alkyl group in all isomeric forms. The term "$C_{(1-4)}$ alkyl" refers to an alkyl group, as defined above, containing at least 1, and at most 4 carbon atoms Examples of such alkyl groups include methyl, ethyl, propyl, iso-propyl, n-butyl, iso-butyl, sec-butyl, or tert-butyl, Examples of such alkoxy groups include methoxy, ethoxy, propoxy, isopropoxy, butoxy, iso-butoxy, sec-butoxy and tert-butoxy.

As used herein, the term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "heteroaryl" represents a 5 or 6 membered unsaturated ring which comprises one or more heteroatoms. When the term heteroaryl represents a 5 membered group it contains a heteroatom selected from O, N or S and may optionally contain a further 1 to 3 nitrogen atoms. When heteroaryl represents a 6-membered group it contains from 1 to 3 nitrogen atoms. Examples of such 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

In one embodiment of the invention,
A is phenyl or pyridyl;
$R^1$ is hydrogen or methyl;
$R^2$ is hydrogen or methyl;
$R^3$ is optionally substituted phenyl;
Y is NH or O;
X is $(CR^4R^5)_n$;
n is 1 or 2; and
$R^4$ and $R^5$ are independently hydrogen or methyl.

In another embodiment of the invention,
A is phenyl;
$R^1$ is hydrogen or methyl;
$R^2$ is hydrogen or methyl
$R^3$ is optionally substituted phenyl:
Y is NH or O: and
X is $(CR^4R^5)_n$;
n is 1 or 2; and
$R^4$ and $R^5$ are both hydrogen.

When $R^3$ is substituted phenyl it may be substituted by one to two substituents selected from fluoro, cyano, trifluoromethyl and methoxy.

In a further embodiment of the invention (piperazinyl) methylene substituent and X are para- to each other across ring A.

In certain of the compounds of formula (I), dependent upon the nature of the substituent there are chiral carbon atoms, such as the carbon atom marked with an "*", and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses. Preferred compounds of formula (I) wherein $R^1$ and $R^2$ are both methyl are those wherein the piperazine C* carbons have the cis configuration.

Certain of the compounds herein can exist in various tautomeric forms and it is to be understood that the invention encompasses all such tautomeric forms.

Suitable compounds of the invention are:
1-[(4-{[(3R,5S)-3,5-dimethyl-1-piperazinyl] methyl}phenyl)acetyl]-N-(4-fluorophenyl)-4-piperidinamine (E1)
N-(3-fluorophenyl)-1-[(4-{[(3S)-3-methyl-1-piperazinyl] methyl}phenyl)acetyl]-4-piperidinamine (E2)
N-(4-fluorophenyl)-1-[(4-{[(3S)-3-methyl-1-piperazinyl] methyl}-phenyl)acetyl]-4-piperidinamine (E3)
3-({1-[(4-{[(3S)-3-methyl-1-piperazinyl]methyl}phenyl) acetyl]-4-piperidinyl}amino)benzonitrile (E4)
4-({1-[(4-{[(3S)-3-methyl-1-piperazinyl]methyl}phenyl) acetyl]-4-piperidinyl}amino)benzonitrile (E5)
N-(3,4-difluorophenyl)-1-[(4-{[(3S)-3-methyl-1-piperazinyl]methyl}-phenyl)acetyl]-4-piperidinamine (E6)
N-[4-fluoro-3-(methyloxy)phenyl]-1-[(4-{[(3S)-3-methyl-1-piperazinyl]methyl}phenyl)acetyl]-4-piperidinamine (E7)
(3S)-1-{[4-(2-{4-[(4-fluorophenyl)oxy]-1-piperidinyl}-2-oxoethyl)phenyl]methyl}-3-methylpiperazine (E8)
(3S)-1-{[4-(2-{4-[(3-fluorophenyl)oxy]-1-piperidinyl}-2-oxoethyl)phenyl]methyl}-3-methylpiperazine (E9)
1-[(4-{[(3S)-3-methyl-1-piperazinyl]methyl}phenyl) acetyl]-N-[3-(trifluoromethyl)phenyl]-4-piperidinamine (E10)

1-[(4-{[(3S)-3-methyl-1-piperazinyl]methyl}phenyl) acetyl]-N-[4-(trifluoromethyl)phenyl]-4-piperidinamine (E11)
N-(3-fluorophenyl)-1-{[4-(1-piperazinylmethyl)phenyl] acetyl}-4-piperidinamine (E12)
N-(3-fluorophenyl)-1-[(4-{[(3R)-3-methyl-1-piperazinyl] methyl}phenyl)acetyl]-4-piperidinamine (E13)
N-(3,4-difluorophenyl)-1-[(4-{[(3R)-3-methyl-1-piperazinyl]methyl}phenyl)acetyl]-4-piperidinamine (E14)
(3R)-1-{[4-(2-{4-[(4-fluorophenyl)oxy]-1-piperidinyl}-2-oxoethyl)phenyl]methyl}-3-methylpiperazine (E15)
(3R)-1-{[4-(2-{4-[(3-fluorophenyl)oxy]-1-piperidinyl}-2-oxoethyl)phenyl]methyl}-3-methylpiperazine (E16)
4-({1-[(4-{[(3R)-3-methyl-1-piperazinyl]methyl}phenyl) acetyl]-4-piperidinyl}oxy)benzonitrile (E17)
4-({1-[(4-{[(3R)-3-methyl-1-piperazinyl]methyl}phenyl) acetyl]-4-piperidinyl}amino)benzonitrile (E18)
3-({1-[(4-{[(3R)-3-methyl-1-piperazinyl]methyl}phenyl) acetyl]-4-piperidinyl}amino)benzonitrile (E19)
1-[(4-{[(3R)-3-methyl-1-piperazinyl]methyl}phenyl) acetyl]-N-[3-(trifluoromethyl)phenyl]-4-piperidinamine (E20)
N-(3-fluorophenyl)-1-[(3-(methyloxy)-4-{[(3S)-3-methyl-1-piperazinyl]methyl}phenyl)acetyl]-4-piperidinamine (E21)
2-fluoro-5-({1-[(4-{[(3S)-3-methyl-1-piperazinyl] methyl}phenyl)acetyl]-4-piperidinyl}amino)benzonitrile (E22)
1-[3-(4-{[(3R,5S)-3,5-dimethyl-1-piperazinyl] methyl}phenyl)propanoyl]-N-(4-fluorophenyl)-4-piperidinamine (E23)
1-[3-(4-{[(3R,5S)-3,5-dimethyl-1-piperazinyl] methyl}phenyl)propanoyl]-N-(3-fluorophenyl)-4-piperidinamine (E24)
N-(4-fluorophenyl)-1-[3-(4-{[(3S)-3-methyl-1-piperazinyl] methyl}phenyl) propanoyl]-4-piperidinamine (E25)
N-(3-fluorophenyl)-1-[3-(4-{[(3S)-3-methyl-1-piperazinyl] methyl}phenyl)propanoyl]-4-piperidinamine (E26)
1-[2-(4-{[(3R,5S)-3,5-dimethyl-1-piperazinyl] methyl}phenyl)propanoyl]-N-(4-fluorophenyl)-4-piperidinamine
1-[2-(4-{[(3R,5S)-3,5-dimethyl-1-piperazinyl] methyl}phenyl)propanoyl]-N-(3-fluorophenyl)-4-piperidinamine (E28)
1-[2-(4-{[(3R,5S)-3,5-dimethyl-1-piperazinyl] methyl}phenyl)-2-methylpropanoyl]-N-(4-fluorophenyl)-4-piperidinamine (E29)
1-[2-(4-{[(3R,5S)-3,5-dimethyl-1-piperazinyl] methyl}phenyl)-2-methylpropanoyl]-N-(3-fluorophenyl)-4-piperidinamine (E30)
(3R,5S)-1-{[4-(2-{4-[(4-fluorophenyl)oxy]-1-piperidinyl}-1,1-dimethyl-2-oxoethyl)phenyl]methyl}-3,5-dimethylpiperazine (E31)
N-(3-fluorophenyl)-1-[3-(5-{[(3S)-3-methyl-1-piperazinyl] methyl}-2-pyridinyl)propanoyl]-4-piperidinamine (E32)
1-[(3-Chloro-4-{[(3S)-3-methyl-1-piperazinyl] methyl}phenyl)acetyl]-N-(3-fluorophenyl)-4-piperidinamine (E33)
N-(2-fluorophenyl)-1-[(4-{[(3R)-3-methyl-1-piperazinyl] methyl}phenyl)acetyl]-4-piperidinamine
N-(3-fluorophenyl)-1-[(5-{[(3S)-3-methyl-1-piperazinyl] methyl}-2-pyridinyl)acetyl]-4-piperidinamine
2-({1-[(4-{[(3R)-3-methyl-1-piperazinyl]methyl}phenyl) acetyl]-4-piperidinyl}amino)benzonitrile
2-fluoro-4-({1-[(4-{[(3S)-3-methyl-1-piperazinyl] methyl}phenyl)acetyl]-4-piperidinyl}amino)benzonitrile hydrochloride The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

In a further aspect, this invention provides processes for the preparation of a compound of formula (I)

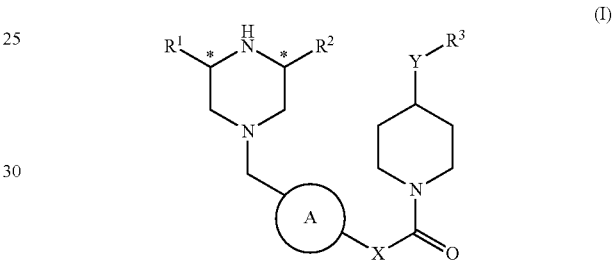

wherein A is phenyl and X is $CH_2$ or a pharmaceutically acceptable salt or solvate thereof, which process comprises reacting of a compound of formula (II)

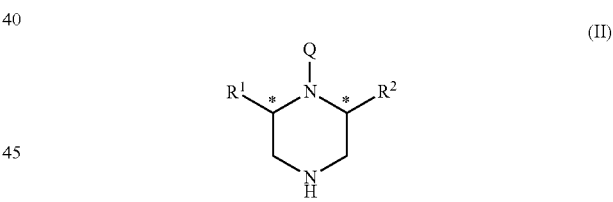

wherein $R^1$ and $R^2$ are as defined in formula (I) and Q is hydrogen or a suitable nitrogen protecting group such as tert-butyloxycarbonyl (BOC) or benzyloxycarbonyl (CBZ), with a compound of formula (III)

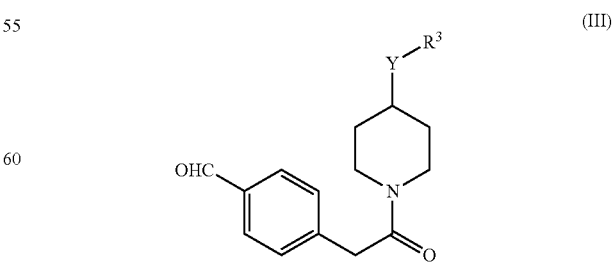

wherein Y and $R^3$ are as defined in formula (I), using reaction conditions suitable for a reductive alkylation, for example in the presence of a reducing agent such as sodium tri(acetoxy)borohydride in a suitable solvent such as dichloromethane or 1,2-dichloroethane.

And thereafter optionally carrying out one or more of the following reactions:
1. Converting one compound of formula (I) into another compound of formula (I);
2. Removing any protecting group;
3. Forming a suitable pharmaceutical acceptable salt or solvate of the compound so formed.

Compounds of formula (III) may be prepared by reacting a compound of formula (IV)

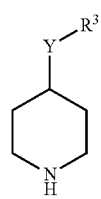

(IV)

wherein $R^3$ and Y are as defined in formula (I), with a compound of formula (V)

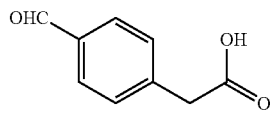

(V)

in the presence of a suitable coupling reagent such as 1-(3-dimethylaminopropyl)-3-ethylcarbodiimide (EDC) or N,N'-dicyclohexylcarbodiimide (DCC), in a suitable solvent such as dichloromethane, dimethylformamide or mixtures thereof.

Alternatively, a compound of formula (III) may be prepared by reacting a compound of formula (IV) with an activated derivative of a compound of formula (V), such as an acid chloride, using general methods described in J. March, *Advanced Organic Chemistry*, 4th Edition, J Wiley & Sons, 1992, p. 417-418.

Compounds of formula (IV), where Y=NH, may be prepared by a reductive alkylation reaction which involves reacting a suitable aniline derivative with a suitably protected piperidin-4-one, such as 1-(tert-butoxycarbonyl)piperidin-4-one, in the presence of a reducing agent such as sodium tri(acetoxy)borohydride, in a solvent such as dichloroethane, followed by removal of the nitrogen protecting group by conventional techniques as described below.

Compounds of formula (IV), where Y=NH, may also be prepared by an arylation reaction which involves reacting a suitable aryl halide with a suitably protected 4-aminopiperidine such as (1-tert-butoxycarbonyl)-4-aminopiperidine, in the presence of a suitable catalyst system such as palladium(II) acetate/BINAP, in a solvent such as 1,4-dioxane, followed by removal of the nitrogen protecting group by conventional techniques as described below.

Compounds of formula (IV), where Y=O, may be prepared by an alkylation reaction which involves reacting a suitable phenol derivative with a suitably protected 4-hydroxypiperidine, such as 1-(tert-butoxycarbonyl)-4-hydroxypiperidine, in the presence of triphenylphosphine and diisopropylazodicarboxylate, in a solvent such as tetrahydrofuran, followed by removal of the nitrogen protecting group by conventional techniques as described below.

Compounds of formula (V) are known or can be prepared using conventional methods. For example, for 4-formylphenylacetic acid, treatment of 4-bromomethylphenylacetic acid with hexamethylenetetramine using methods similar to those described in J. March, *Advanced Organic Chemistry*, 4th Edition, J Wiley & Sons, 1992, p. 1194.

The present invention provides a further process for the preparation of a compound of formula (I) wherein A is phenyl and X is $CH_2$ or a pharmaceutically acceptable salt or solvate thereof, which process comprises reacting a compound of formula (VI)

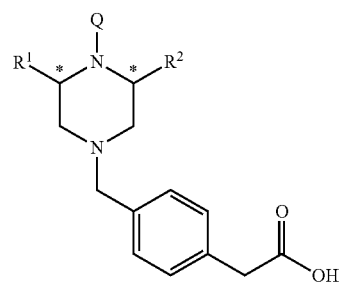

(VI)

wherein $R^1$ and $R^2$ are as defined in formula (I) and Q is hydrogen or a suitable nitrogen protecting group such as tert-butyloxycarbonyl (BOC) or benzyloxycarbonyl (CBZ), with a compound of formula (IV) in the presence of a suitable coupling reagent such as 1-(3-dimethylaminopropyl)-3-ethylcarbodiimide (EDC) or N,N'-dicyclohexylcarbodiimide (DCC), in a suitable solvent such as dichloromethane, dimethylformamide or mixtures thereof.

And thereafter optionally carrying out one or more of the following reactions:
1. Converting one compound of formula (I) into another compound of formula (I);
2. Removing any protecting group;
3. Forming a suitable pharmaceutical acceptable salt or solvate of the compound so formed.

Alternatively, a compound of formula (I) wherein A is phenyl and X is $CH_2$ or a pharmaceutically acceptable salt or solvate thereof, may be prepared by a process which comprises reacting an activated derivative of a compound of formula (VI), such as an acid chloride, with a compound of formula (IV) using general methods described in J. March, *Advanced Organic Chemistry*, 4th Edition, J Wiley & Sons, 1992, p. 417-418

And thereafter optionally carrying out one or more of the following reactions:
1. Converting one compound of formula (I) into another compound of formula (I);
2. Removing any protecting group;
3. Forming a suitable pharmaceutical acceptable salt or solvate of the compound so formed.

Compounds of formula (VI) may be prepared by conventional hydrolysis and decarboxylation of a compound of formula (VII)

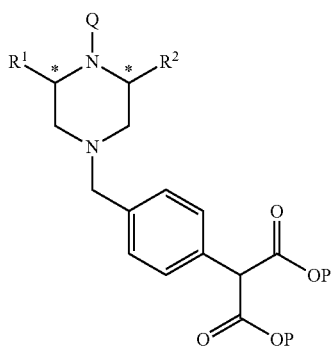

(VII)

wherein $R^1$ and $R^2$ are as defined in formula (I), Q is hydrogen or a suitable nitrogen protecting group such as tert-butyloxycarbonyl (BOC) or benzyloxycarbonyl (CBZ) and P is a suitable alkyl group such as methyl or ethyl, using aqueous sodium hydroxide in a suitable solvent such as 1,4-dioxane followed by acidification and decarboxylation by heating in a suitable solvent such as toluene.

Compounds of formula (VII) may be prepared by reaction of a compound of formula (VIII)

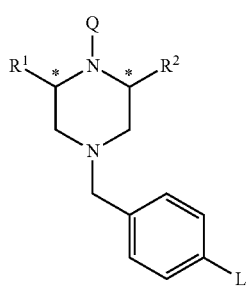

(VIII)

wherein $R^1$ and $R^2$ are as defined in formula (I), L is a suitable leaving group such as a halogen, for example bromine, and Q is hydrogen or a suitable nitrogen protecting group such as tert-butyloxycarbonyl (BOC) or benzyloxycarbonyl (CBZ), with a suitable dialkyl malonate such as diethyl malonate under palladium catalysis in a suitable solvent such as 1,4-dioxane at reflux using a method similar to that described in S. L. Buchwald et al, J. Am. Chem. Soc., 2000, vol 122, p 1360-1370

Compounds of formula (VIII) may be prepared by reaction of a compound of formula (IX)

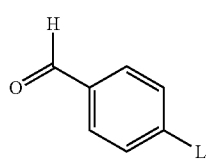

(IX)

wherein L is halogen, with a compound of formula (II), using reaction conditions suitable for a reductive amination, for example in the presence of a reducing agent such as sodium tri(acetoxy)borohydride in a suitable solvent such as dichloromethane or 1,2-dichloroethane.

Compounds of formula (VI) may also be prepared by conventional hydrolysis of a compound of formula (X)

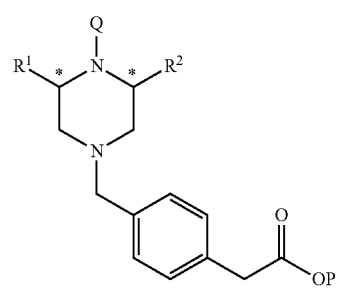

(X)

wherein $R^1$ and $R^2$ are as defined in formula (I), Q is hydrogen or a suitable nitrogen protecting group such as tert-butyloxycarbonyl (BOC) or benzyloxycarbonyl (CBZ), and P is a suitable alkyl group such as methyl, using a suitable base such as aqueous sodium hydroxide in a suitable solvent such as tetrahydrofuran or 1,4-dioxane.

Compounds of formula (X) may be prepared by reacting a compound of formula (II) with a compound of formula (XI),

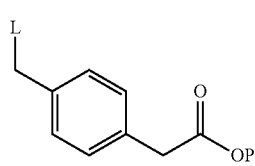

(XI)

wherein P is a suitable alkyl group such as methyl and L is a suitable leaving group such as a halogen, for example bromine, in the presence of a suitable base such as diisopropylethylamine in a suitable solvent such as dimethylformamide.

Compounds of formula (XI) wherein P is methyl may be prepared by reaction of a compound of formula (XII),

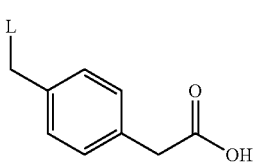

(XII)

wherein L is a halogen such as bromine, with methanol in the presence of trimethylsilyl chloride. Compounds of formula (XII) are commercially available.

The present invention provides a process for the preparation of a compound of formula (I) wherein A is substituted phenyl and X is $CH_2$ or a pharmaceutically acceptable salt or solvate thereof, which process comprises reacting a compound of formula (XIII),

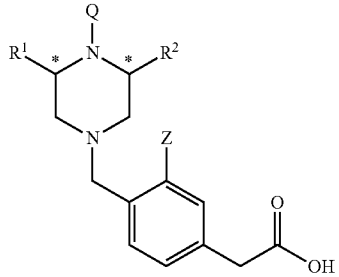

(XIII)

wherein $R^1$ and $R^2$ are as defined in formula (I), Z is $C_{(1-4)}$ alkoxy and Q is hydrogen or a suitable nitrogen protecting group such as tert-butyloxycarbonyl (BOC) or benzyloxycarbonyl (CBZ) with a compound of formula (IV) in the presence of a suitable coupling reagent such as 1-(3-dimethylaminopropyl)-3-ethylcarbodiimide (EDC) or N-dicyclohexyl carbodiimide (DCC), in a suitable solvent such as dichloromethane, dimethylformamide or mixtures thereof.

And thereafter optionally carrying out one or more of the following reactions:
1. Converting one compound of formula (I) into another compound of formula (I);
2. Removing any protecting group;
3. Forming a suitable pharmaceutical acceptable salt or solvate of the compound so formed.

Alternatively, a compound of formula (I) wherein A is substituted phenyl and X is $CH_2$ or a pharmaceutically acceptable salt or solvate thereof, may be prepared by a process which comprises reacting an activated derivative of a compound of formula (XIII), such as an acid chloride, with a compound of formula (IV) using general methods described in J. March, *Advanced Organic Chemistry*, 4th Edition, J Wiley & Sons, 1992, p. 417-418.

And thereafter optionally carrying out one or more of the following reactions:
1. Converting one compound of formula (I) into another compound of formula (I);
2. Removing any protecting group;
3. Forming a suitable pharmaceutical acceptable salt or solvate of the compound so formed.

Compounds of formula (XIII) may be prepared by conventional hydrolysis and decarboxylation of a compound of formula (XIV)

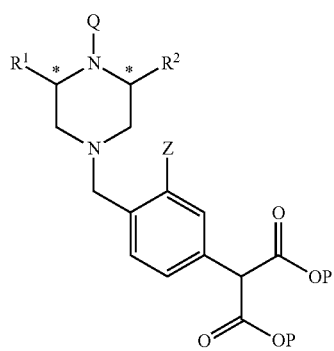

(XIV)

wherein $R^1$ and $R^2$ are as defined in formula (I), Q is hydrogen or a suitable nitrogen protecting group such as tert-butyloxycarbonyl (BOC) or benzyloxycarbonyl (CBZ), Z is $C_{(1-4)}$ alkoxy and P is a suitable alkyl group such as methyl or ethyl, using aqueous sodium hydroxide followed by acidification and decarboxylation by heating in a suitable solvent such as tetrahydrofuran or 1,4-dioxane.

Compounds of formula (XIV) may be prepared by reaction of a compound of formula (XV),

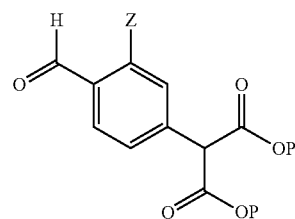

(XV)

wherein Z is $C_{(1-4)}$alkoxy and P is a suitable alkyl group such as methyl or ethyl, with a compound of formula (II) using reaction conditions suitable for a reductive amination, for example in the presence of a reducing agent such as sodium tri(acetoxy)borohydride in a suitable solvent such as dichloromethane or 1,2-dichloroethane.

Compounds of formula (XV) may be prepared by conventional hydrolysis of a compound of formula (XVI),

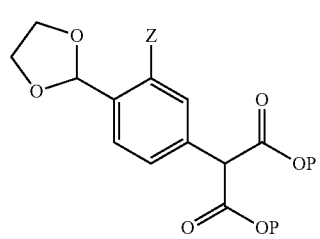

(XVI)

wherein Z is $C_{(1-4)}$alkoxy and P is alkyl such as ethyl, using a suitable aqueous acid, such as dilute hydrochloric acid, in a suitable solvent such as tetrahydrofuran.

Compounds of formula (XVI) may be prepared by reacting a compound of formula (XVII)

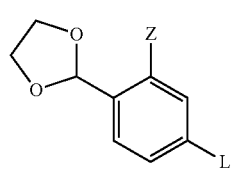

(XVII)

wherein L is halogen such as bromine and Z is $C_{(1-4)}$alkoxy, with a suitable dialkyl malonate such as diethyl malonate under palladium catalysis in a suitable solvent such as 1,4-dioxane at reflux using a method similar to that described in S. L. Buchwald et al, *J. Am. Chem. Soc.*, 2000, vol 122, p 1360-1370.

Compounds of formula (XVII) may be prepared according to the procedure described in A. Tromelin et al, European Journal of Medicinal Chemistry, 1986, vol 21(5), p 397-402.

The present invention provides a process for the preparation of a compound of formula (I) wherein A is phenyl and X is $CMe_2$ or a pharmaceutically acceptable salt or solvate thereof, which process comprises reacting a compound of formula (XVIII)

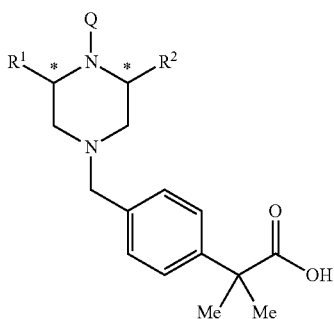

(XVIII)

wherein $R^1$ and $R^2$ are as defined in formula (I) and Q is hydrogen or a suitable nitrogen protecting group such as tert-butyloxycarbonyl (BOC) or benzyloxycarbonyl (CBZ) with a compound of formula (IV) in the presence of a suitable coupling reagent such as 1-(3-dimethylaminopropyl)-3-ethylcarbodiimide (EDC) or N,N'-dicyclohexylcarbodiimide (DCC), in a suitable solvent such as dichloromethane, dimethylformamide or mixtures thereof.

And thereafter optionally carrying out one or more of the following reactions:

1. Converting one compound of formula (I) into another compound of formula (I);
2. Removing any protecting group;
3. Forming a suitable pharmaceutical acceptable salt or solvate of the compound so formed.

Alternatively, a compound of formula (I) wherein A is phenyl and X is $CMe_2$ or a pharmaceutically acceptable salt or solvate thereof, may be prepared by a process which comprises reacting an activated derivative of a compound of formula (XVIII), such as an acid chloride, with a compound of formula (IV) using general methods described in J. March, *Advanced Organic Chemistry*, 4$^{th}$ Edition, J Wiley & Sons, 1992, p. 417-418.

And thereafter optionally carrying out one or more of the following reactions:

1. Converting one compound of formula (I) into another compound of formula (I);
2. Removing any protecting group;
3. Forming a suitable pharmaceutical acceptable salt or solvate of the compound so formed.

Compounds of formula (XVIII) may be prepared by conventional hydrolysis of a compound of formula (XIX)

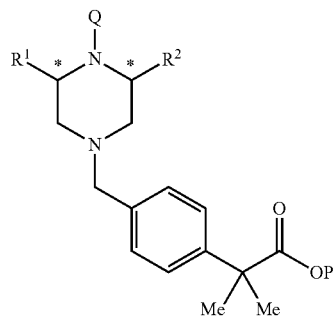

(XIX)

wherein $R^1$ and $R^2$ are as defined in formula (I), Q is hydrogen or a suitable nitrogen protecting group such as tert-butyloxycarbonyl (BOC) or benzyloxycarbonyl (CBZ), and P is a suitable alkyl group such as methyl, using a suitable base such as aqueous lithium hydroxide in a suitable solvent such as 1,4-dioxane.

Compounds of formula (XIX) may be prepared by reacting a compound of formula (VIII) with a compound of formula (XX)

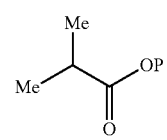

(XX)

wherein P is a suitable alkyl group such as methyl using a procedure similar to that described in J. F. Hartwig et al, J. Am. Chem. Soc., 2002, vol 124, p 12557-12565. The reaction may be carried out in the presence of a suitable base such as lithium di(cyclohexyl)amide, a suitable catalyst system such as bis(dibenzylidene) palladium (0)/tri(tert-butyl)phosphine and in a suitable solvent such as toluene.

The present invention provides a process for the preparation of a compound of formula (I) wherein A is phenyl and X is CHMe or a pharmaceutically acceptable salt or solvate thereof, which process comprises reacting a compound of formula (XXI)

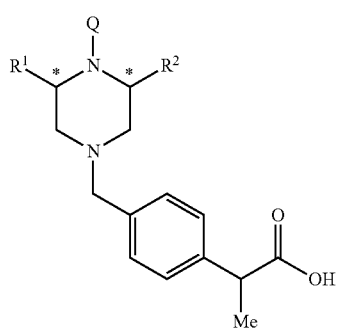

(XXI)

wherein $R^1$ and $R^2$ are as defined in formula (I) and Q is hydrogen or a suitable nitrogen protecting group such as tert-butyloxycarbonyl (BOC) or benzyloxycarbonyl (CBZ) with a compound of formula (IV) in the presence of a suitable coupling reagent such as 1-(3-dimethylaminopropyl)-3-ethylcarbodiimide (EDC) or N,N'-dicyclohexylcarbodiimide (DCC), in a suitable solvent such as dichloromethane, dimethylformamide or mixtures thereof.

And thereafter optionally carrying out one or more of the following reactions:
1. Converting one compound of formula (I) into another compound of formula (I);
2. Removing any protecting group;
3. Forming a suitable pharmaceutical acceptable salt or solvate of the compound so formed.

Alternatively, a compound of formula (I) wherein A is phenyl and X is CHMe or a pharmaceutically acceptable salt or solvate thereof, may be prepared by a process which comprises reacting an activated derivative of a compound of formula (XXI), such as an acid chloride, with a compound of formula (IV) using general methods described in J. March, *Advanced Organic Chemistry*, 4$^{th}$ Edition, J Wiley & Sons, 1992, p. 417-418.

And thereafter optionally carrying out one or more of the following reactions:
1. Converting one compound of formula (I) into another compound of formula (I);
2. Removing any protecting group;
3. Forming a suitable pharmaceutical acceptable salt or solvate of the compound so formed.

Compounds of formula (XXI) may be prepared by conventional hydrolysis and decarboxylation of a compound of formula (XXII)

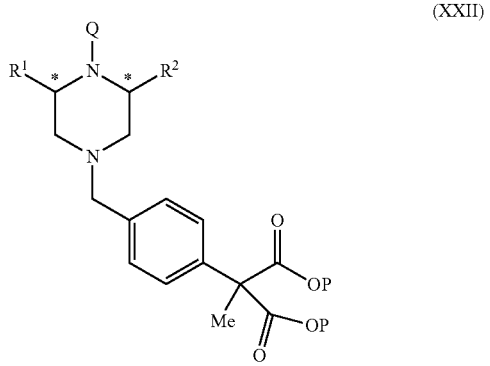

wherein R$^1$ and R$^2$ are as defined in formula (I), Q is hydrogen or a suitable nitrogen protecting group such as tert-butyloxycarbonyl (BOC) or benzyloxycarbonyl (CBZ) and P is a suitable alkyl group such as methyl or ethyl, using aqueous sodium hydroxide followed by acidification and decarboxylation by heating in a suitable solvent such as 1,4-dioxane or tetrahydrofuran.

Compounds of formula (XXII) may be prepared from a compound of formula (VII)

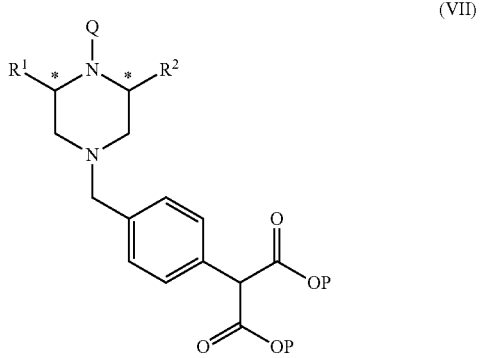

wherein R$^1$ and R$^2$ are as defined in formula (I), Q is hydrogen or a suitable nitrogen protecting group such as tert-butyloxycarbonyl (BOC) or benzyloxycarbonyl (CBZ) and P is a suitable alkyl group such as methyl or ethyl, using standard alkylation conditions. For example reaction with a suitable base such as sodium hydride together with a suitable methylating agent such as iodomethane, in a suitable solvent, for example dimethylformamide.

The present invention provides a process for the preparation of a compound of formula (I) wherein A is phenyl and X is CH$_2$CH$_2$ or a pharmaceutically acceptable salt or solvate thereof, which process comprises reacting a compound of formula (XXIII)

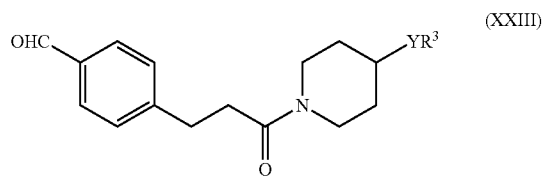

wherein Y and R$^3$ are as defined in formula (I), with a compound of formula (II) using reaction conditions suitable for a reductive amination, for example in the presence of a reducing agent such as sodium tri(acetoxy)borohydride in a suitable solvent such as dichloromethane or 1,2-dichloroethane.

And thereafter optionally carrying out one or more of the following reactions:

1. Converting one compound of formula (I) into another compound of formula (I);

2. Removing any protecting group;

3. Forming a suitable pharmaceutical acceptable salt or solvate of the compound so formed.

Compounds of formula (XXIII) may be prepared by reacting a compound of formula (XXIV)

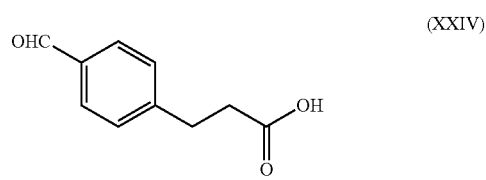 [SMILES: O=Cc1ccc(CCC(=O)O)cc1]

with a compound of formula (IV) in the presence of a suitable coupling reagent such as 1-(3-dimethylaminopropyl)-3-ethylcarbodiimide (EDC) or N,N'-dicyclohexylcarbodiimide (DCC), in a suitable solvent such as dichloromethane, dimethylformamide or mixtures thereof.

Alternatively, a compound of formula (XXIII) may be prepared by reacting a compound of formula (IV) with an activated derivative of a compound of formula (XXIV), such as an acid chloride, using general methods described in J. March, *Advanced Organic Chemistry*, 4$^{th}$ Edition, J Wiley & Sons, 1992, p. 417-418.

The present invention provides a process for the preparation of a compound of formula (I) wherein A is 2,5-pyridyl and X is CH$_2$CH$_2$ or a pharmaceutically acceptable salt or solvate thereof, which process comprises hydrogenation of a compound of formula (XXV),

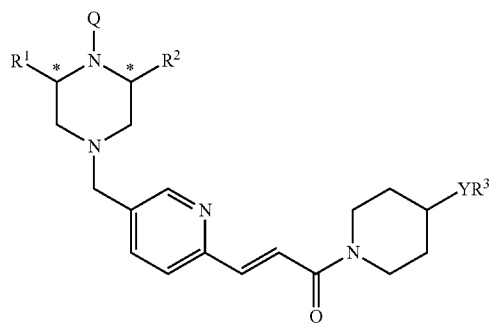
(XXV)

wherein R¹ and R² are as defined in formula (I) and Q is a suitable protecting group such as tert-butyloxycarbonyl (BOC) or benzyloxycarbonyl (CBZ) in the presence of a suitable catalyst such as palladium black and in a suitable solvent such as methanol.

And thereafter optionally carrying out one or more of the following reactions:

1. Converting one compound of formula (I) into another compound of formula (I);
2. Removing any protecting group;
3. Forming a suitable pharmaceutical acceptable salt or solvate of the compound so formed.

Compounds of formula (XXV) may be prepared by reacting a compound of formula (XXVI)

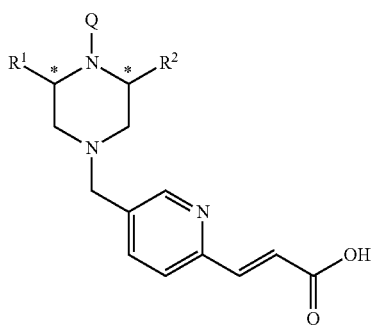
(XXVI)

wherein R¹ and R² are as defined in formula (I) and Q is a suitable protecting group such as tert-butyloxycarbonyl (BOC) or benzyloxycarbonyl (CBZ), with a compound of formula (IV) in the presence of a suitable coupling reagent such as 1-(3-dimethylaminopropyl)-3-ethylcarbodiimide (EDC) or N,N'-dicyclohexylcarbodiimide (DCC), in a suitable solvent such as dichloromethane, dimethylformamide or mixtures thereof.

Alternatively, a compound of formula (XXV) may be prepared by reacting a compound of formula (IV) with an activated derivative of a compound of formula (XXVI), such as an acid chloride, using general methods described in J. March, *Advanced Organic Chemistry*, 4$^{th}$ Edition, J Wiley & Sons, 1992, p. 417-418.

Compounds of formula (XXVI) may be prepared by conventional hydrolysis of a compound of formula (XXVII)

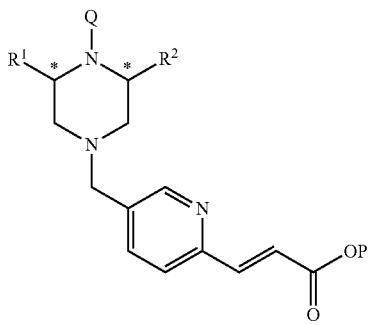
(XXVII)

wherein R¹ and R² are as defined in formula (I), Q is a suitable protecting group such as tert-butyloxycarbonyl (BOC) or benzyloxycarbonyl (CBZ), and P is a suitable alkyl group such as methyl, using a suitable base such as aqueous lithium hydroxide in a suitable solvent such as 1,4-dioxane.

Compounds of formula (XXVII) may be prepared by reacting a compound of formula (XXVIII)

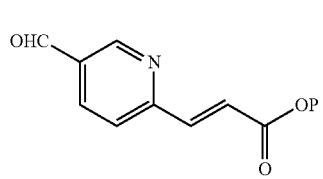
(XXVIII)

wherein P is a suitable alkyl group such as methyl, with a compound of formula (II) using reaction conditions suitable for a reductive amination, for example in the presence of a reducing agent such as sodium tri(acetoxy)borohydride in a suitable solvent such as dichloromethane or 1,2-dichloroethane.

Compounds of formula (XXVIII) may be prepared by reacting a compound of formula (XXIX)

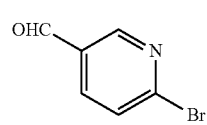
(XXIX)

with a suitable alkyl acrylate such as methyl acrylate at elevated temperature, for example under microwave conditions, in the presence of a suitable catalyst system such as allyl palladium (II) chloride dimer/tri(o-tolyl)phosphine, and a suitable base, such as sodium acetate. A suitable solvent is dimethylformamide.

It will be appreciated by those skilled in the art that it may be necessary to protect certain reactive substituents during some of the above procedures. Standard protection and deprotection techniques, such as those described in Greene T. W. Protective groups in organic synthesis, New York, Wiley (1981), can be used. For example, primary amines can be protected as phthalimide, trifluoroacetyl, benzyl, tert-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as tert-butyloxycarbonyl may be removed using an acid such as hydrochloric or trifluoroacetic acid in a suitable solvent such as dichloromethane, diethylether, 1,4-dioxane, isopropanol or mixtures thereof.

Pharmaceutically acceptable salts may be prepared conventionally by reaction with the appropriate acid or acid derivative.

The present invention also provides compounds of formula (III), (VI), (VII), (X), (XIII), (XIV), (XVIII), (XIX), (XXI), (XXII), (XXIII), (XXV), (XXVI) and (XXVII) as shown above wherein Y, $R^1$, $R^2$ and $R^3$ are as defined for formula (I), Q is hydrogen or a suitable protecting group such as tert-butyloxycarbonyl (BOC) or benzyloxycarbonyl (CBZ) and P is a suitable alkyl group such as ethyl. These compounds are useful as intermediates in the preparation of compounds of the present invention.

The potencies and efficacies of the compounds of this invention for GPR38 can be determined by FLIPR assay performed on the human cloned receptor as described herein. Compounds of formula (I) have demonstrated partial or full agonist activity at the GPR38 receptor, using the FLIPR (FLourometric Imaging Plate Reader) functional assay described herein.

Compounds of formula (I) and their pharmaceutically acceptable salts are therefore of use in the treatment of conditions or disorders which are mediated via the GPR38 receptor. In particular the compounds of formula (I) and their pharmaceutically acceptable salts are of use in the treatment of certain gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, Crohn's disease, colitis, cachexia associated with advanced diseases such as cancer and/or the treatment thereof, appetite/metabolism related cachexia and other disorders such as incontinence (herein after referred to as the "Disorders of the Invention").

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions or disorders mediated via the GPR38 receptor. In particular the invention provides a compound of formula (I) or a pharmaceutically acceptable salt thereof for use as a therapeutic substance in the treatment of gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, Crohn's disease, colitis, cachexia associated with advanced diseases such as cancer and/or the treatment thereof, appetite/metabolism related cachexia and other disorders such as incontinence. The invention further provides a method of treatment of conditions or disorders in mammals including humans which can be mediated via the GPR38 receptor, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the GPR38 receptor In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, 1.0 to 500 mg or 1.0 to 200 mg and such unit doses may be administered more than once a day, for example two or three times a day. Such therapy may extend for a number of weeks or months.

The compounds of the present invention may be used in combination preparations. For example, the compounds of the invention may be used in combination with one or more compounds with activity in reducing gastric acid; one or more compounds with activity in reducing gastro-esophageal reflux; one or more compounds with activity in reducing esophago-gastric irritancy or inflammation, especially when used to alleviate erosive or non-erosive esophagitis; one or more compounds with analgesic activity; and/or one or more compounds with mixed activity on motility and pain.

Examples of compounds with activity in reducing gastric acid include H2 receptor antagonists, acid pump antagonists and proton pump inhibitors. Examples of compounds with activity in reducing gastro-esophageal reflux include agonists at GABA-B. Examples of compounds with analgesic activity include compounds active at Neurokinin receptors (NK1, 2, 3), TRPV1 and sodium-channels. Examples of compounds with mixed activity on motility and pain include CRF2 antagonists, 5-HT3 antagonists or octreotide or other molecules active at sst2 receptors.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.
Conditions. Hardware and Software for Analytical LCMS Systems
Hardware
Agilent 1100 Gradient Pump
Agilent 1100 Autosampler
Agilent 1100 DAD Dectector
Agilent 1100 Degasser
Agilent 1100 Oven
Agilent 1100 Controller
Waters ZQ Mass Spectrometer
Sedere Sedex 55, Sedere Sedex 85 or Polymer Labs PL-ELS-2100
Software
Waters MassLynx version 4.0 SP2
Column The column used is a Waters Atlantis, the dimensions of which are 4.6 mm×50 mm. The stationary phase particle size is 3 μm.
Solvents
A: Aqueous solvent=Water+0.05% Formic Acid
B: Organic solvent=Acetonitrile+0.05% Formic Acid
Method The generic method used has a 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

Flow Rate

The above method has a flow rate of 3 ml/mins
Patent Information for Open Access Mass Directed Auto Prep System (MDAP)
Hardware Open Access Mass Directed Prep instruments consist of the following:
1 Waters 600 Gradient pump
1 Waters 2767 inject/collector
1 Waters Reagent manager
1 MicroMass ZQ Mass Spectrometer
1 Gilson Aspec—waste collector 1 Gilson 115 post-fraction UV detector
1 Computer System.
Software
MicroMass MassLynx v4.0
Column The column used is typically a Supelco LCABZ++ column whose dimensions are 20 mm internal diameter by 100 mm in length. The stationary phase particle size is 5 μm.
Solvents
A: Aqueous solvent=Water+0.1% Formic Acid
B: Organic solvent=MeCN:Water 95:5+0.05% Formic Acid
Make up solvent=MeOH:Water 80:20+50 mMol Ammonium Acetate
Needle rinse solvent=MeOH:Water:DMSO 80:10:10
Methods One of five methods may be used depending on the analytical retention time of the compound of interest.

All have a 15-minute runtime, which comprises of a 10-minute gradient followed by a 5-minute column flush and re-equilibration step.
MDP 1.5-2.2=0-30% B
MDP 2.0-2.8=5-30% B
MDP 2.5-3.0=15-55% B
MDP 2.8-4.0=30-80% B
MDP 3.8-5.5=50-90% B
Flow Rate All of the above methods have a flow rate of 20 ml/min.
Conditions Used for NMR
Hardware
Bruker 400 MHz Ultrashield
Bruker B-ACS60 Autosampler
Bruker Advance 400 Console
Bruker DPX250
Bruker AVANCE 500
Bruker DRX600
Software
User interface—NMR Kiosk
Controlling software—XWin NMR version 3.0
Chromatography Unless stated otherwise, all chromatography was carried out using silica columns
Abbreviations
HCl—hydrochloric acid, hydrogen chloride
NaHCO$_3$—sodium hydrogen carbonate
Na$_2$SO—sodium sulfate
1,2-DCE—1,2-dichloroethane,
NaOH—sodium hydroxide
DCM—dichloromethane
DMF—N,N-dimethylformamide
THF—tetrahydrofuran
MeOH—methanol,
EtOAc—ethyl acetate
MgSO$_4$—magnesium sulfate
NH$_3$-ammonia
TFA—trifluoroacetic acid
Et$_2$O—diethyl ether
CDCl$_3$-deuterochloroform
DCC—N,N'-dicyclohexylcarbodiimide
BINAP—(±)-2,2'-bis(diphenylphosphino)-1,1'-binaphthalene Description 1

1,1-Dimethylethyl
4-[(4-fluorophenyl)amino]-1-piperidinecarboxylate
(D1)

A solution of 1,1-dimethylethyl 4-oxo-1-piperidinecarboxylate (1 g, 5 mmol), 4-fluoroaniline (0.56 g, 5 mmol) and acetic acid (0.26 ml, 5 mmol) in 1,2-DCE (30 ml) was stirred at room temperature for 24 h. Sodium tri(acetoxy)borohydride (1.48 g, 7 mmol) was then added and stirring continued for 24 h. The reaction mixture was washed with water, dried (MgSO$_4$) and then concentrated in vacuo to give the title compound as a crude solid (1.6 g). δ$_H$(CDCl$_3$, 250 MHz) 6.88 (2H, t), 6.54 (2H, dd), 4.04 (2H, m), 3.35 (1H, m), 2.91 (2H, m), 2.02 (2H, m), 1.46 (9H, s), 1.30 (2H, m).

Description 2

N-(4-Fluorophenyl)-4-piperidinamine (D2)

A solution of D1 (1.6 g) in 2M HCl (5 ml) and 1,4-dioxane (20 ml) was heated at 60° C. for 24 h. On cooling, the solution was diluted with water, basified with 2M NaOH solution and extracted with EtOAc (×3). The combined organics were dried (MgSO$_4$) and concentrated in vacuo to give the title compound as a yellow oil (0.719). δ$_H$(CDCl$_3$, 250 MHz) 6.88 (2H, t), 6.54 (2H, dd), 3.30 (1H, m), 3.20 (2H, m), 2.70 (2H, m), 2.05 (2H, m), 1.62 (2H, Br), 1.29 (2H, m).

Description 3

(4-Formylphenyl)acetic Acid (D3)

The title compound was prepared from [4-(bromomethyl)phenyl]acetic acid and hexamethylenetetramine using a method similar to that described in J. March, *Advanced Organic Chemistry*, 4$^{th}$ Edition, J Wiley & Sons, 1992, p. 1194.

Description 4

4-(2-{4-[(4-Fluorophenyl)amino]-1-piperidinyl}-2-oxoethyl)benzaldehyde (D4)

A mixture of D3 (87 mg, 0.53 mmol), D2 (102 mg, 0.53 mmol), 1-(3-dimethylaminopropyl)-3-ethylcarbodiimide hydrochloride (123 mg, 0.64 mmol), and 1-hydroxybenzotriazole (98 mg, 0.64 mmol) in DMF (2 ml) was stirred at room temperature overnight. The DMF was removed in vacuo then EtOAc and water were added. The product was extracted into EtOAc and the combined organic layers were washed with saturated aq. NaHCO$_3$ solution (×2) and brine then dried (Na$_2$SO$_4$). The solvent was removed in vacuo and the resulting residue was purified by chromatography eluting with an EtOAc/petroleum ether gradient to afford the title compound (149 mg). MS (ES): MH$^+$ 341.

Description 5a 1,1-Dimethylethyl
4-[(3-fluorophenyl)amino]-1-piperidinecarboxylate
(D5a)

A solution of 1,1-dimethylethyl 4-oxo-1-piperidinecarboxylate (1.91 g, 9.53 mmol), 3-fluoroaniline (1.06, 9.53 mmol) and acetic acid (0.55 ml, 9.53 mmol) in 1,2-DCE (50 ml) was stirred at room temperature overnight. Sodium tri(acetoxy)borohydride (2.82 g, 13.3 mmol) was then added, stirred for 8 hrs and then allowed to stand at room temperature. The reaction mixture was diluted with DCM and washed with NaHCO$_3$ solution, dried over MgSO$_4$ and then concentrated to give the product which was purified by column chromatography. Elution with 0-40% EtOAc/pentane gave the title compound as a white solid (2.3 g). δ$_H$ (CDCl$_3$, 250

MHz) 7.08 (1H, q), 6.35 (3H, m), 4.04 (1H, br s), 3.65 (1H, br s), 3.38 (1H, m), 2.92 (2H, m), 2.02 (2H, m), 1.47 (9H, s), 1.34 (2H, m).

Description 5b

N-(3-Fluorophenyl)-4-piperidinamine (D5b)

A solution of D5a (2.91 g) in 2M HCl (5 ml) and 1,4-dioxane (40 ml) was heated at 70° C. with stirring overnight. On cooling, the solvent was removed in vacuo and the residue diluted with 2M NaOH solution and extracted with 9:1 EtOAc/$^t$BuOH (×2). The organics were dried (MgSO$_4$) and concentrated in vacuo to give the title compound as a yellow solid (1.33 g). $\delta_H$ (CDCl$_3$, 250 MHz) 7.07 (1H, q), 6.33 (3H, m), 3.83 (1H, br s), 3.33 (1H, br s), 3.12 (2H, m), 2.71 (2H, m), 2.04 (2H, m), 1.30 (2H, m).

Description 6

Phenylmethyl (2S)-4-[(4-bromophenyl)methyl]-2-methyl-1-piperazine Carboxylate (D6)

A mixture of 4-bromobenzaldehyde (1.19 g, 6.42 mmol), phenylmethyl (2S)-2-methyl-1-piperazinecarboxylate (1.505 g, 6.42 mmol) and sodium triacetoxyborohydride (2.04 g, 9.63 mmol) in 1,2-DCE (15 ml) was stirred at room temperature overnight. Saturated aq. NaHCO$_3$ solution was added and the mixture stirred for 30 mins. Product was extracted and the extracts dried (Na$_2$SO$_4$). Chromatography (0-30% EtOAc in pentane) gave the title compound (2.18 g). MS (ES): MH$^+$ 403/405.

Description 7

Diethyl {4-[((3S)-3-methyl-4-{[(phenylmethyl)oxy]carbonyl}-1-piperazinyl)methyl]phenyl}propanedioate (D7)

A mixture of D6 (1.62 g, 4 mmol), diethyl malonate (0.73 ml, 4.8 mmol), palladium (II) acetate (27 mg, 0.12 mmol), potassium phosphate (1.95 g, 2.3 mmol) and bis(1,1-dimethylethyl)(2'-methyl-2-biphenylyl)phosphane (83 mg, 0.264 mmol) in 1,4-dioxane (20 ml) were refluxed together under argon for ~20 h. The mixture was filtered through Celite® and concentrated. Chromatography (0-40% EtOAc/hexane) gave the title compound as a clear oil (1.165 g). MS (ES): MH$^+$ 483.

Description 8

{4-[((3S)-3-Methyl-4-{[(phenylmethyl)oxy]carbonyl}-1-piperazinyl)methyl]phenyl}acetic Acid (D8)

A mixture of D7 (761 mg, 1.58 mmol), 2M NaOH solution (6 ml) and 1,4-dioxane (6 ml) was stirred at room temperature for 2 h. The solvents were removed and the residue dissolved in water and the pH adjusted to 4 with 2M HCl. The product was extracted with EtOAc and the combined extracts were dried and concentrated. The product was refluxed in toluene (~20 ml) for 2 h and the solvent was evaporated to give the title compound as a yellow foam (505 mg). MS (ES): MH$^+$ 383, (M–H)$^-$ 381.

Description 9a 1,1-Dimethylethyl 4-[(3,4-difluorophenyl)amino]-1-piperidinecarboxylate (D9a)

The title compound was prepared from 1,1-dimethylethyl 4-oxo-1-piperidinecarboxylate and 3,4-difluoroaniline using a method similar to that described for D1 although the crude product was purified by chromatography.

Description 9b

N-(3,4-Difluorophenyl)-4-piperidinamine (D9b)

The title compound was prepared from D9a using a method similar to that described for D2 although the reaction was heated at 80° C.

Description 10a 1,1-Dimethylethyl 4-[(3-cyanophenyl)amino]-1-piperidinecarboxylate (D10a)

A mixture of BINAP (560 mg, 0.9 mmol), palladium acetate (135 mg, 0.6 mmol) and cesium carbonate (2.932 g, 9 mmol) in 1,4-dioxane (10 ml) was sonicated for 50 minutes. 1,1-Dimethylethyl 4-amino-1-piperidinecarboxylate (1.2 g, 6 mmol) and 3-bromobenzonitrile (1.638 g, 9 mmol) were added and the mixture heated to 105° C. overnight under an argon atmosphere. On cooling, the solvent was removed in vacuo and the residue partitioned between water (100 ml) and EtOAc (100 ml). The organic layer was separated, dried and concentrated and the crude product purified by chromatography. Elution with a 0-50% Et$_2$O/petroleum ether gradient gave the title compound as a white solid (1.49 g). $\delta_H$ (CDCl$_3$, 250 MHz) 7.22 (2H, t), 6.95 (1H, dd), 6.77 (2H, m), 4.07 (2H, m), 3.77 (1H, m), 3.41 (1H, m), 3.20 (1H, m), 2.93 (2H, m), 2.03 (2H, m), 1.47 (9H, s), 1.34 (2H, m). MS (ES): MH$^+$ 302.

Description 10b 3-(4-Piperidinylamino)benzonitrile (D10b)

A solution of D10a (750 mg, 2.43 mmol) in DCM (30 ml) was cooled in an ice bath and TFA (6 ml) was added. The reaction mixture was then stirred at room temperature for 1 h. The solvent was removed in vacuo and the residue loaded onto an Isolute SCX cartridge. Elution with MeOH (100 ml) followed by 2M NH$_3$ in MeOH (100 ml) gave the title compound as a white solid (613 mg). $\delta_H$ (CDCl$_3$, 250 MHz) 7.21 (2H, t), 6.93 (1H, m), 6.77 (2H, m), 3.78 (1H, m), 3.35 (1H, m), 3.14 (2H, m), 2.73 (2H, m), 2.06 (2H, m), 1.34 (2H, m). MS (ES): MH$^+$ 202.

Description 11a 1,1-Dimethylethyl [(4-cyanophenyl)amino]-1-piperidinecarboxylate (D11a)

The title compound was prepared from 1,1-dimethylethyl 4-amino-1-piperidinecarboxylate and 4-bromobenzonitrile using a method similar to that described for D10a

Description 11b 4-(4-Piperidinylamino)benzonitrile (D11b)

The title compound was prepared from D11a using a method similar to that described for D10b although purification by chromatography was also carried out.

Description 12a 1,1-Dimethylethyl 4-{[4-fluoro-3-(methyloxy)phenyl]amino}-1-piperidinecarboxylate (D12a)

The title compound was prepared from 1,1-dimethylethyl 4-oxo-1-piperidinecarboxylate and 4-fluoro-3-methoxyaniline using a method similar to that described for D1.

Description 12b

N-[4-Fluoro-3-(methyloxy)phenyl]-4-piperidinamine (D12b)

The title compound was prepared from D12a using a method similar to that described for D2 although the reaction was heated at 80° C.

Description 13

1,1-Dimethylethyl 4-[(3-fluorophenyl)oxy]-1-piperidinecarboxylate (D13)

To a solution of 1,1-dimethylethyl 4-hydroxy-1-piperidinecarboxylate (24 g, 112 mmol), 3-fluorophenol (5.6 g, 59 mmol) and triphenylphosphine (31.4 g, 118 mmol) in THF (100 ml) was added di-isopropylazodicarboxylate (23.3 ml, 118 mmol). The reaction was stirred at room temperature for 3 days and then the solvent removed in vacuo. The residue was diluted with DCM, hexane was added and the resultant white precipitate filtered off. The filtrate was concentrated in vacuo and purified by chromatography. Elution with DCM gave the title compound (16.4 g, 87% pure). $\delta_H$ (CDCl$_3$, 250 MHz) 1.47 (9H, s), 1.76 (2H, m), 1.92 (2H, m), 3.35 (2H, ddd), 3.69 (2H, ddd), 4.44 (1H, m), 6.65 (3H, m), 7.20 (1H, m).

Description 14

4-[(3-Fluorophenyl)oxy]piperidine (D14)

A solution of D13 (16.4 g, 55 mmol) in DCM (200 ml) at 0° C. was treated drop-wise with TFA (17 ml). The reaction was warmed to room temperature for 2.5 hrs and left overnight. The solvent was then removed in vacuo and the residue partitioned between DCM and 2M NaOH solution. The aqueous was further extracted with DCM (×2) and the combined organics concentrated in vacuo. The residue was redissolved in DCM and extracted with 2M HCl (×2) which was then basified and re-extracted with DCM. The combined organics were concentrated in vacuo to give the title compound (12 g). $\delta_H$ (CDCl$_3$, 250 MHz) 1.66 (2H, m), 2.01 (2H, m), 2.73 (2H, m), 3.14 (2H, m), 4.34 (1H, m), 6.68 (3H, m), 7.19 (1H, m), MS (ES): MH$^+$ 196. This whole was diluted with MeOH and treated with 1M HCl in Et$_2$O to give the hydrochloride salt of the title compound (8.0 g).

Description 15

4-[(4-Fluorophenyl)oxy]piperidine (D15)

The title compound may be prepared using a method similar to that described in L. C Blumberg, M. F. Brown, M. M. Hayward and C. S. Poss, PCT Int. Appl., WO 2004009550.

Description 16

Methyl [4-(bromomethyl)phenyl]acetate (D16)

To a solution of 4-(bromomethyl)phenylacetic acid (20 g, 87.3 mmol) in MeOH (200 ml) was added trimethylsilylchloride (2 ml) and the reaction stirred for 2 h. The solvent was removed in vacuo and the residue was twice re-dissolved in MeOH (200 ml) and re-concentrated to give the title compound (21.08 g). $\delta_H$ (CDCl$_3$, 250 MHz) 7.36 (2H, d), 7.26 (2H, d), 4.49 (2H, s), 3.69 (3H, s), 3.62 (2H, s).

Description 17

1,1-Dimethylethyl (2S)-2-methyl-4-({4-[2-(methyloxy)-2-oxoethyl]phenyl}methyl)-1-piperazinecarboxylate (D17)

To a solution of D16 (20.8 g, 85.6 mmol) and diisopropylethylamine (16.4 ml, 94.1 mmol) in dry DMF (100 ml) was added a solution of 1,1-dimethylethyl (2S)-2-methyl-1-piperazinecarboxylate (18.8 g, 94.1 mmol) in dry DMF (75 ml) with cooling in an ice bath. The reaction was warmed to room temperature and stirred for 15 mins. The solvent was removed in vacuo and the residue partitioned between EtOAc and 2M NaOH solution (400 ml, 1:1). The organic phase was washed with water (200 ml) and brine (200 ml) and the combined aqueous washings were back extracted with EtOAc (200 ml). The EtOAc extracts were combined, dried (MgSO$_4$) and concentrated in vacuo to give the crude product which was purified by chromatography. Elution with 20-25% EtOAc/hexane gave the title compound as a colourless oil (29.3 g). $\delta_H$ (CDCl$_3$, 250 MHz) 7.29 (2H, d), 7.22 (2H, d), 4.18 (1H, m), 3.74 (1H, m), 3.69 (3H, s), 3.62 (2H, s), 3.51 (1H, d), 3.39 (1H, d), 3.10 (1H, td), 2.75 (1H, m), 2.59 (1H, m), 2.12 (1H, dd), 1.99 (1H, m), 1.45 (9H, s), 1.24 (3H, d).

Description 18

{4-[((3S)-4-{[(1,1-Dimethylethyl)oxy]carbonyl}-3-methyl-1-piperazinyl)methyl]phenyl}acetic Acid (D18)

To a solution of D17 (29.3 g, 80.9 mmol) in THF (200 ml) was added 2M NaOH solution (100 ml) and the two phase reaction mixture stirred at room temperature for 3 h. The mixture was concentrated in vacuo to remove the THF and the aqueous solution was extracted with EtOAc (2×100 ml). The aqueous phase was acidified to pH6 with conc. HCl and extracted with DCM (3×300 ml). The combined organics were washed with brine (×2), dried and concentrated in vacuo to give the title compound as a colourless foam (27.8 g). $\delta_H$ (CDCl$_3$, 400 MHz) 7.27 (2H, d), 7.23 (2H, d), 4.20 (1H, m), 3.81 (1H, m), 3.62 (2H, s), 3.59 (1H, d), 3.49 (1H, d), 3.15

(1H, m), 2.88 (1H, m), 2.69 (1H, m), 2.20 (1H, dd), 2.05 (1H, m), 1.45 (9H, s), 1.25 (3H, d).

Description 19

1,1-Dimethylethyl (2S)-4-{[4-(2-{4-[(3-fluorophenyl)amino]-1-piperidinyl}-2-oxo-ethyl)phenyl]methyl}-2-methyl-1-piperazinecarboxylate (D19)

A mixture of D18 (27.8 g, 79.8 mmol), N-[3-(dimethylamino)propyl]-N'-ethylcarbodiimide hydrochloride (22.9 g, 119.7 mmol), 1-hydroxybenzotriazole hydrate (16.2 g, 119.7 mmol), triethylamine (45 ml, 319.1 mmol) and D56b hydrochloride salt (18.4 g, 79.8 mmol) in dry DMF (400 ml) was stirred at room temperature overnight. The solvent was removed in vacuo and the residue re-dissolved in DCM (300 ml), washed with 2M NaOH (2×200 ml), water (200 ml) and brine (200 ml). All aqueous washings were combined and back extracted with DCM (2×100 ml). The combined organics were dried and concentrated to give a solid which was purified by chromatography (silica pre-washed with 50% EtOAc/hexane). Elution with 70% EtOAc/hexane gave the title compound as a white solid (34.95 g). $\delta_H$ (CDCl$_3$, 400 MHz) 7.28 (2H, d), 7.19 (2H, d), 7.07 (1H, t), 6.23-6.40 (3H, m), 4.52 (1H, m), 4.17 (1H, m), 3.78-3.88 (2H, m), 3.74 (2H, s), 3.60 (1H, d), 3.40 (1H, d), 3.43 (1H, m), 3.38 (1H, d), 3.06-3.17 (2H, m), 2.89 (1H, m), 2.74 (1H, m), 2.57 (1H, m), 1.94-2.13 (4H, m), 1.45 (9H, s), 1.32 (1H, m), 1.21 (3H, d), 1.09 (1H, m). MS (ES) MH$^+$ 525.

Description 20

1,1-Dimethylethyl 4-{[3-(trifluoromethyl)phenyl]amino}-1-piperidinecarboxylate (D20)

A Solution of 1,1-Dimethylethyl 4-Oxo-1-Piperidinecarboxylate (0.5 g, 2.5 mmol), 3-(trifluoromethyl)aniline (0.402 g, 2.5 mmol) and sodium tri(acetoxy)borohydride (0.80 g, 3.75 mmol) in 1,2-DCE (5 ml) was stirred at room temperature, under argon overnight. Saturated aq. NaHCO$_3$ solution (15 ml) was added and stirring continued for 1 h. The reaction mixture was extracted with DCM and the organic phase concentrated in vacuo. Recrystallisation of the solid residue gave the title compound as a white solid (0.86 g). $\delta_H$ (CDCl$_3$, 250 MHz)) 7.25 (1H, t), 6.92 (1H, d), 6.75 (2H, m), 4.06 (2H, m), 3.45 (1H, m), 2.94 (2H, m), 2.04 (2H, m), 1.46 (9H, s), 1.36 (2H, m).

Description 21

N-[3-(Trifluoromethyl)phenyl]-4-piperidinamine (D21)

A solution of two combined preparations of D20 (0.86 g, 2.5 mmol) in DCM (40 ml) was treated with TFA (10 ml) and the reaction stirred at room temperature, under argon for 2 h. The solvent was removed in vacuo and the residue partitioned between DCM and water. The aqueous was basified to pH14 with 2M NaOH solution then extracted with EtOAc (×5). The combined organics were dried (Na$_2$SO$_4$) and concentrated in vacuo to give the title compound as a transparent oil (0.64 g). $\delta_H$(CDCl$_3$, 250 MHz) 7.24 (1H, t), 6.90 (1H, d), 6.74 (2H, m), 3.75 (1H, m), 3.40 (1H, m), 3.14 (2H, m), 2.74 (2H, m), 2.07 (2H, m), 1.34 (2H, m).

Description 22

1,1-Dimethylethyl 4-{[4-(trifluoromethyl)phenyl]amino}-1-piperidinecarboxylate (D18)

The title compound was prepared from 1,1-dimethylethyl 4-oxo-1-piperidinecarboxylate and 4-trifluoromethylaniline using a method similar to that described for D20

Description 23

N-[4-(Trifluoromethyl)phenyl]-4-piperidinamine (D23)

The title compound was prepared from D22 using a method similar to that described for D21.

Description 24

Phenylmethyl 4-[(4-bromophenyl)methyl]-1-piperazinecarboxylate (D24)

The title compound was prepared from phenylmethyl 1-piperazinecarboxylate and 4-bromobenzaldehyde using a method to that described for D6

Description 25

Diethyl {4-[(4-{[(phenylmethyl)oxy]carbonyl}-1-piperazinyl)methyl]phenyl}propanedioate (D25)

The title compound was prepared from D24 using a method similar to that described for D7.

Description 26

{4-[(4-{[(Phenylmethyl)oxy]carbonyl}-1-piperazinyl)methyl]phenyl}acetic Acid (D26)

A solution of D25 (304 mg, 0.65 mmol) in 2M NaOH solution (10 ml) and THF (10 ml) was stirred at room temperature for 1 h then 40° C. for 1 h. 2M HCl was added to adjust the solution to pH6 followed by heating to 60° C. overnight. The solvent was removed in vacuo and the residue partitioned between water and EtOAc. The organic extract was dried and concentrated to give the title compound (145 mg). MS (ES): MH$^+$ 369, (M−H)$^-$ 367.

Description 27

Phenylmethyl (2R)-2-methyl-4-({4-[2-(methyloxy)-2-oxoethyl]phenyl}methyl)-1-piperazinecarboxylate (D27)

A mixture of D16 (243 mg, 1 mmol), diisopropylethylamine (174 ul, 1 mmol) 1,1-dimethylethyl (2R)-2-methyl-1-piperazinecarboxylate (234 mg, 1 mmol) in DMF was stirred at room temperature for 1 h then allowed to stand overnight. The solvent was removed in vacuo, then the residue was diluted with water (20 ml) and extracted with EtOAc (2×20 ml). The combined organic extracts were dried (MgSO$_4$) and concentrated in vacuo to give the title compound as a yellow oil (383 mg). $\delta_H$ (CDCl$_3$, 250 MHz) 7.21-7.40 (9H, m), 5.13 (2H, AB), 4.29 (1H, m), 3.91 (1H, m), 3.70 (3H, s), 3.62 (2H, s), 3.43 (2H, m), 3.20 (1H, m), 2.78 (1H, m), 2.62 (1H, m), 2.05-2.18 (2H, m), 1.29 (3H, d).

Description 28

{4-[((3R)-3-Methyl-4-{([(phenylmethyl)oxy]carbonyl}-1-piperazinyl)methyl]phenyl}acetic Acid (D28)

A solution of D27 (380 mg, 0.96 mmol) in THF (4 ml) and 2M NaOH solution (1 ml) was stirred at room temperature overnight. Water (10 ml) was added and the solution washed with EtOAc (20 ml). The aqueous phase was adjusted to pH6 and extracted with EtOAc (2×20 ml). The combined extracts were washed with brine, dried ($MgSO_4$) and concentrated in vacuo to give the title compound as a colourless gum (255 mg). $\delta_H$ ($CDCl_3$, 250 MHz) 7.20-7.40 (9H, m), 5.12 (2H, AB), 4.29 (1H, m), 3.91 (1H, d), 3.61 (2H, s), 3.51 (2H, AB), 3.20 (1H, m), 2.85 (1H, d), 2.69 (1H, d), 2.20 (1H, m), 2.10 (1H, m), 1.29 (3H, m).

Description 29

Phenylmethyl (2R)-4-{[4-(2-{4-[(3-fluorophenyl)amino]-1-piperidinyl}-2-oxoethyl)phenyl]methyl}-2-methyl-1-piperazinecarboxylate (D29)

A mixture of D28 (100 mg, 0.261 mmol), N-[3-(dimethylamino)propyl]-N'-ethylcarbodiimide hydrochloride (75 mg, 0.392 mmol), 1-hydroxybenzotriazole (53 mg, 0.392 mmol), triethylamine (110 ul, 0.784 mmol) and D5b hydrochloride salt (60 mg, 0.261 mmol) in DMF (2 ml) was stirred at room temperature for 3 days. The solvent was removed in vacuo and the residue was purified by chromatography. Elution with 0-10% MeOH/DCM gave the title compound as a colourless oil (136 mg). $\delta_H$ ($CDCl_3$, 400 MHz) 7.31-7.38 (5H, m), 7.28 (2H, d), 7.19 (2H, d), 7.07 (1H, t), 6.23-6.39 (3H, m), 5.13 (2H, AB), 4.52 (1H, m), 4.27 (1H, br s), 3.88 (2H, m), 3.74 (2H, s), 3.62 (1H, br s), 3.44 (3H, m), 3.16 (2H, m), 2.88 (1H, m), 2.76 (1H, d), 2.59 (1H, d), 1.94-2.15 (4H, m), 1.32 (1H, m), 1.26 (3H, m), 1.08 (1H, m). MS (ES): $MH^+$ 559.

Description 30

1,1-Dimethylethyl 4-[(4-cyanophenyl)oxy]-1-piperidinecarboxylate (D30)

The title compound was prepared from 4-hydroxybenzonitrile and 1,1-dimethylethyl 4-hydroxy-1-piperidinecarboxylate using a method similar to that described for D13.

Description 31

4-(4-Piperidinyloxy)benzonitrile (D31)

The title compound was prepared from D30 using a method similar to that described for D14.

Description 32

2-[4-Bromo-2-(methyloxy)phenyl]-1,3-dioxolane (D32)

The title compound may be prepared using the method described in A. Tromelin, P. Demerseman, R. Royer, P. Gayral and J. Fourniat, European Journal of Medicinal Chemistry 1986, 21(5), 397-402.

Description 33

Diethyl [4-(1,3-dioxolan-2-yl)-3-(methyloxy)phenyl]propanedioate (D33)

A mixture of D32 (200 mg, 0.81 mmol), diethyl malonate (155 mg, 0.97 mmol), palladium (II) acetate (5.4 mg, 0.024 mmol), potassium phosphate (395 mg, 2 mmol) and bis(1,1-dimethylethyl)(2'-methyl-2-biphenylyl)phosphane (16.6 mg, 0.053 mmol) in dry 1,4-dioxane (10 ml) was heated at 120° C. under argon for 7 h. Aqueous work-up (water/EtOAc) followed by purification by chromatography (50% $Et_2O$/petroleum ether) gave title compound (191 mg). $\delta_H$ ($CDCl_3$, 400 MHz) 7.51 (1H, d), 6.99 (2H, m), 6.14 (1H, s), 4.60 (1H, s), 4.23 (4H, m), 4.12 (2H, m), 4.04 (4H, m), 3.88 (3H, s), 1.24 (6H, t). MS (ES): $MH^+$ 339.

Description 34

Diethyl [4-formyl-3-(methyloxy)phenyl]propanedioate (D34)

A solution of D33 (191 mg, 0.56 mmol) in THF (5 ml) and 2M HCl (5 ml) was stirred at room temperature for 1 h. The solvent was removed in vacuo and aqueous work-up (water/EtOAc) gave the title compound (149 mg). $\delta_H$ ($CDCl_3$, 400 MHz) 10.45 (1H, s), 7.81 (1H, d), 7.11 (1H, s), 7.04 (1H, d), 4.64 (1H, s), 4.23 (4H, m), 3.95 (3H, s), 1.27 (6H, t). MS (ES): $MH^+$ 295.

Description 35

Diethyl [4-[((3S)-4-{[(1,1-dimethylethyl)oxy]carbonyl}-3-methyl-1-piperazinyl)methyl]-3-(methyloxy)phenyl]propanedioate (D35)

The title compound was prepared from D34 and 1,1-dimethylethyl (2S)-2-methyl-1-piperazinecarboxylate using a method similar to that described for D6.

Description 36

[4-[((3S)-4-{[(1,1-Dimethylethyl)oxy]carbonyl}-3-methyl-1-piperazinyl)methyl]-3-(methyloxy)phenyl]acetic acid (D36)

The title compound was prepared from D35 using a method similar to that described for D26.

Description 37

1,1-Dimethylethyl (2S)-4-{[4-(2-{4-[(3-fluorophenyl)amino]-1-piperidinyl}-2-oxoethyl)-2-(methyloxy)phenyl]methyl}-2-methyl-1-piperazinecarboxylate (D37)

A mixture of D36 (90 mg, 0.24 mmol), polymer-supported DCC (225 mg, 1.6 mmol/g, 0.36 mmol), D5b (46 mg, 0.24 mmol) and 1-hydroxybenzotriazole (49 mg, 0.36 mmol) in DMF (9 ml) and DCM (3 ml) was stirred at room temperature overnight. Scavenger resins (PS-trisamine, PS-isocyanate and MP-carbonate) were added and the mixture was stirred for 2 h and then filtered. Purification by chromatography gave the title compound (42 mg). MS (ES): MH+ 555.

Description 38

1,1-Dimethylethyl 4-[(3-cyano-4-fluorophenyl)amino]-1-piperidinecarboxylate (D38)

The title compound was prepared from 5-bromo-2-fluorobenzonitrile and 1,1-dimethylethyl 4-amino-1-piperidinecarboxylate using a method similar to that described for D10a.

Description 39

2-Fluoro-5-(4-piperidinylamino)benzonitrile (D39)

The title compound was prepared from D38 using a method similar to that described for D10b.

Description 40

1,1-Dimethylethyl (2S)-4-{[4-(2-{4-[(3-cyano-4-fluorophenyl)amino]-1-piperidinyl}-2-oxoethyl)phenyl]methyl}-2-methyl-1-piperazinecarboxylate (D40)

The title compound was prepared from D8 and D39 using a method similar to that described for D29 although the reaction time was overnight and an aqueous work-up (DCM/water) was carried out prior to chromatography.

Description 41

4-(3-{4-[(4-Fluorophenyl)amino]-1-piperidinyl}-3-oxopropyl)benzaldehyde (D41)

Step 1: (2E)-3-(4-formylphenyl)-2-propenoic acid (2.55 g) was dissolved in EtOH (250 ml) and hydrogenated at atmospheric pressure with 10% Pd/C (0.8 g) as catalyst. After 5 h the reaction mixture was filtered and concentrated to give a 1:1 mixture of 3-[4-(hydroxymethyl)phenyl]propanoic acid and 3-(4-methylphenyl)propanoic acid (2.43 g).
Step 2: The acid mixture from step 1 (500 mg), N-[3-(dimethylamino)propyl]-N -(ethylcarbodiimide hydrochloride (723 mg, 3.78 mmol), 1-hydroxybenzotriazole (578 mg, 3.78 mmol) in DMF (10 ml) was treated with D2 (561 mg, 2.9 mmol) and the mixture stirred at room temperature for 2 h. The DMF was removed in vacuo and EtOAc and water were added. The aqueous was extracted with EtOAc and the combined organics were washed with saturated aq. NaHCO$_3$ solution and brine, then dried (Na$_2$SO$_4$) and concentrated to give a mixture of [4-(3-{4-[(4-fluorophenyl)amino]-1-piperidinyl}-3-oxopropyl)phenyl]methanol and N-(4-fluorophenyl)-1-[3-(4-methylphenyl)propanoyl]-4-piperidinamine (1.1 g).
Step 3: This whole was dissolved in DCM (20 ml) and treated with manganese dioxide (2 g). After stirring overnight, further manganese dioxide was added (5 g) and stirring continued for 30 mins. The mixture was filtered, concentrated and purified by chromatography (10-90% EtOAc/pentane) to give the title compound as a yellow gum (282 mg). MS (ES): MH+ 355.

Description 42

4-(3-{4-[(3-Fluorophenyl)amino]-1-piperidinyl}-3-oxopropyl)benzaldehyde (D42)

The title compound was prepared from D5b using a method similar to that described for D41.

Description 43

1,1-Dimethylethyl (2R,6S)-4-[(4-bromophenyl)methyl]-2,6-dimethyl-1-piperazinecarboxylate (D43)

A mixture of 4-bromobenzaldehyde (1.85 g, 10 mmol), 1,1-dimethylethyl (2R,6S)-2,6-dimethyl-1-piperazinecarboxylate (2.15 g, 10 mmol) and sodium triacetoxyborohydride (3.18 g) in 1,2-DCE (35 ml) was stirred at room temperature for 3 days. Saturated aq. NaHCO$_3$ solution was added and the mixture stirred for 30 mins. The product was extracted into EtOAc and the extracts dried (Na$_2$SO$_4$) and concentrated. The residue was dissolved in DCM and treated with PS-hydrazine resin with stirring for 2 h. The resin was removed by filtration and the solvent removed in vacuo. Chromatography (0-40% EtOAc/hexane) gave the title compound (3.52 g). MS (ES): MH+ 383/385.

Description 44

Diethyl {4-[((3S)-4-{[(1,1-dimethylethyl)oxy]carbonyl}-3-methyl-1-piperazinyl)methyl]phenyl}propanedioate (D44)

The title compound was prepared from D43 using a method similar to that described for D7.

Description 45

Diethyl {4-[((3S)-4{[(1,1-dimethylethyl)oxy]carbonyl}-3-methyl-1-piperazinyl)methyl]phenyl}(methyl)propanedioate (D45)

A solution of D44 (538 mg, 1.16 mmol) in DMF (10 ml) was added dropwise to sodium hydride (61 mg, 60% w/w in oil, 1.51 mmol) in DMF (2 ml) at 0° C. under argon. After stirring for 10 mins, methyl iodide (0.144 ml, 2.32 mmol) was added and the reaction mixture allowed to warm to room temperature over 1 h. Ammonium chloride solution was added and the mixture extracted with EtOAc. The extracts were washed with saturated aq. NaHCO$_3$ solution and water, then dried (Na$_2$SO$_4$) and concentrated in vacuo. Chromatography eluting with 0-10% EtOAc/hexane gave the title compound as a clear gum (356 mg). MS (ES): MH+ 477.

Description 46

2-{4-[((3S)-4{[(1,1-Dimethylethyl)oxy]carbonyl}-3-methyl-1-piperazinyl)methyl]phenyl}propanoic Acid (D46)

A solution of D45 (356 mg, 1.34 mmol) in 2M NaOH solution (3 ml) and 1,4-dioxane (3 ml) was stirred at room temperature for 1 h then 80° C. for 3 h. The solvents were removed in vacuo, water was added and the mixture adjusted to pH4 with 2M HCl. The product was extracted into EtOAc and the extracts were washed with brine then dried (Na$_2$SO$_4$) and concentrated to give the title compound (256 mg). $\delta_H$ (CDCl$_3$, 400 MHz) 7.32 (2H, d), 7.27 (2H, d), 4.10 (2H, m), 3.74 (1H, q), 3.49 (2H, br s), 2.64 (2H, m), 2.14 (2H, m), 1.52 (3H, d), 1.46 (9H, s), 1.30 (6H, d). MS (ES): MH$^+$ 377, (M–H$^+$) 375.

Description 47

1,1-Dimethylethyl (2R,6S)-4-({4-[1,1-dimethyl-2-(methyloxy)-2-oxoethyl]phenyl}methyl)-2,6-dimethyl-1-piperazinecarboxylate (D47)

A solution of methyl 2-methylpropanoate (188 ul, 1.64 mmol) in toluene (3 ml) was added to lithium dicyclohexylamide (362 mg, 1.93 mmol) under glove bag conditions. The suspension was stirred for 10 mins then added to a mixture of D43 (570 mg, 1.49 mmol) and bis(dibenzylideneacetone) palladium (0) (43 mg, 0.074 mmol). Tri(tert-butyl)phosphine (18 ul, 0.074 mmol) was added and the reaction mixture stirred at room temperature overnight. The solvent was removed in vacuo and chromatography eluting with 0-90% EtOAc/petroleum ether gave the title compound as a yellow oil (395 mg). $\delta_H$ (CDCl$_3$, 250 MHz) 7.29 (4H, m), 4.07 (2H, m), 3.66 (3H, s), 3.46 (2H, s), 2.61 (2H, m), 2.12 (2H, dd), 1.58 (6H, s), 1.46 (9H, s), 1.29 (6H, d). MS (ES): MH$^+$ 405.

Description 48

2-{4-[((3R,5S)-4-{[(1,1-Dimethylethyl)oxy]carbonyl}-3,5-dimethyl-1-piperazinyl)methyl]phenyl}-2-methylpropanoic Acid (D48)

A mixture of D47 (395 mg, 0.978 mmol) and lithium hydroxide monohydrate (82 mg, 1.95 mmol) in water (5 ml) and 1,4-dioxane (10 ml) was stirred at room temperature for 3 days. The solvents were removed in vacuo and the residue dissolved in water. The solution was washed with ether, acidified to pH4 with 1M HCl then extracted with DCM (×2). The combined organics were dried (Na$_2$SO$_4$) and concentrated in vacuo to give the title compound as a yellow foam (316 mg). $\delta_H$ (CDCl$_3$, 250 MHz) 7.35 (4H, m), 4.11 (2H, br), 3.71 (2H, br), 2.67 (2H, br), 2.17 (2H, br), 1.61 (6H, s), 1.46 (9H, s), 1.33 (6H, br d). MS (ES): MH$^+$ 391, (M–H$^+$) 389.

Description 49

Ethyl (2E)-3-(5-formyl-2-pyridinyl)-2-propenoate (D49)

A mixture of 2-bromo-5-formylpyridine (500 mg, 2.6 mmol), methyl acrylate (0.6 ml, 6.5 mmol), tri-(o-tolyl)phosphine (80 mg, 0.26 mmol), allyl palladium (II) chloride dimer (47 mg, 0.13 mmol) and sodium acetate (1.08 g, 8 mmol) in DMF (10 ml) was heated at 170° C. in a microwave reactor for 0.75 h. The reaction mixture was filtered through Celite® then diluted with DCM and water. The organic phase was dried, concentrated in vacuo and purified by chromatography to give the title compound as a white solid (50 mg). $\delta_H$ (CDCl$_3$, 250 MHz) 10.14 (1H, s), 9.09 (1H, d), 8.19 (1H, dd), 7.72 (1H, d), 7.57 (1H, d), 7.08 (1H, d), 3.85 (3H, s). MS (ES): MH$^+$ 192.

Description 50

Phenylmethyl (2S)-4-({6-[(1E)-3-(ethyloxy)-3-oxo-1-propen-1-yl]-3-pyridinyl}methyl)-2-methyl-1-piperazinecarboxylate (D50)

The title compound was prepared from D49 and phenylmethyl (2S)-2-methyl-1-piperazinecarboxylate using a method similar to that described for D6

Description 51

(2E)-3-{5-[((3S)-3-methyl-4-{[(phenylmethyl)oxy]carbonyl}-1-piperazinyl)methyl]-2-pyridinyl}-2-propenoic Acid (D51)

The title compound was prepared from D50 using a method similar to that described for D48 although the reaction time was 3 h.

Description 52

Phenylmethyl (2S)-4-{[6-((1E)-3-{4-[(3-fluorophenyl)amino]-1-piperidinyl}-3-oxo-1-propen-1-yl)-3-pyridinyl]methyl}-2-methyl-1-piperazinecarboxylate (D52)

The title compound was prepared from D51 and D5b using a method similar to that described for D37.

Description 53

1,1-Dimethylethyl (2S)-4-({2-chloro-4-[2-(methyloxy)-2-oxoethyl]phenyl}methyl)-2-methyl-1-piperazinecarboxylate (D53)

The title compound was prepared from methyl (3-chloro-4-formylphenyl)acetate (Epple, R. et al., PCT Int. Appl. WO2005116000) and 1,1-dimethylethyl (2S)-2-methyl-1-piperazinecarboxylate hydrochloride using a method similar to that described for D6 with the addition of triethylamine (1.1 eq) to the reaction mixture and a reaction time of ~3 days.

Description 54

{3-Chloro-4-[((3S)-4-{[(1,1-dimethylethyl)oxy]carbonyl}-3-methyl-1-piperazinyl)methyl]phenyl}acetic Acid (D54)

The title compound was prepared from D53 using a method similar to that described for D48 with a reaction time of 4 h.

Description 55

1,1-Dimethylethyl (2S)-4-{[2-chloro-4-(2-{4-[(3-fluorophenyl)amino]-1-piperidinyl}-2-oxoethyl)phenyl]methyl}-2-methyl-1-piperazinecarboxylate (D55)

The title compound was prepared from D54 and D5b using a procedure similar to that described for D37 with the reaction carried out under an argon atmosphere.

Description 56

N-(3-Fluorophenyl)-4-piperidinamine hydrochloride (D56)

3-Fluoroaniline (28.38 ml, 0.296 mol) was added to a solution of 4-oxo-1-piperidine carboxylate (60 g, 0.302 mol) in 1,2-DCE (600 ml) and the mixture stirred for 15 mins. Sodium tri(acetoxy)borohydride (83 g, 0.392 mol) was added gradually over 5 mins and the mixture stirred for 5.5 hrs then poured into a mixture of 2 M HCl (100 ml), water (200 ml) and ice (1 l). The phases were separated and the aqueous phase extracted with DCM (200 ml). The combined organic phases were dried over MgSO$_4$ and concentrated to give a pale yellow solid which was dissolved in MeOH (400 ml) and treated with 2M HCl (100 ml). The resulting solution was stirred at 60° C. overnight. 5M HCl (100 ml) was added and heating continued for a further 7 h. The reaction mixture was concentrated in vacuo to give a yellow oily solid. This was recrystallised from MeOH/EtOAc to give two batches of the title compound (42.6 g & 17.0 g). These batches were then recrystallised from IMS/EtOAc and the resulting batches were dried in vacuo at 50° C. to give the title compound (49.0 g total). $\delta_H$ (MeOD, 250 MHz) 7.54 (1H, q), 7.24 (2H, m), 7.15 (1H, t), 3.89 (1H, m), 3.54 (2H, d), 3.11 (2H, t), 2.24 (2H, d), 2.01 (2H, m).

Description 57

1,1-Dimethylethyl 4-[(3-fluorophenyl)amino]-1-piperidinecarboxylate (D57)

Sodium triacetoxyborohydride (NaBH(OAc)$_3$ 74 g, 0.35 mol) was added to a stirred solution of 1,1-Dimethylethyl 4-oxo-1-piperidinecarboxylate (50 g, 0.25 mol) and 3-Fluoroaniline (24 ml, 0.25 mol) in isopropyl acetate (1-PrOAc, 500 ml) and the slurry stirred overnight.

Description 58

N-(3-Fluorophenyl)-4-piperidinamine (D58)

Water (250 ml) was added to the slurry formed in D57, the mixture stirred and warmed to 30-35° C. and the layers separated.

5M Aqueous sulphuric acid (75 ml) was added and the mixture stirred at 50-55° C. for 5 h. Water (250 ml) was added, the mixture cooled to 30-35° C. and the layers separated.

The aqueous solution was diluted with tert-butylmethyl ether (TBME, 250 ml), the mixture was stirred for 1 min and basified to pH 12-14 by cautious addition of 32% w/w aqueous NaOH (140 g, 100 ml), keeping the temperature between 30 and 35° C. The layers were separated and the aqueous extracted with fresh TBME (250 ml). The combined organic extracts were washed at 25 to 35° C. with 20% w/v aq. NaCl (200 ml) the aqueous layer separated off and the organic solution distilled down at atmospheric pressure to a final volume of about 200 ml and cooled to 50° C. Iso-octane (250 ml) was added slowly at 45-50° C. and the heating bath was removed and the reaction mixture cooled to 20-25° C. The solution was stirred at 20-25° C. overnight. Iso-octane (250 ml) was added, the slurry heated to 40° C. and distilled in vacuo down to a final volume of 250 ml maintaining the temperature between 30 and 40° C. The final slurry was cooled to 0-5° C. (in ice-water), stirred for 40 min, filtered, the solids washed with iso-octane (2×100 ml) and dried in vacuo at 44° C. for 3 hrs to give the title product (33.5 g). $\delta_H$ (DMSO-d$_6$, 400 MHz) 7.04 (1H, q), 6.40 (1H, m), 6.31 (1H, m), 6.23 (1H, m), 5.77 (1H, d), 3.50-2.60 (1H br s), 3.23 (1H, m), 2.93 (2H, m), 2.55 (2H, m), 1.85 (2H, m), 1.20 (2H, m).

Description 59

{4-[((3S)-4-{[(1,1-Dimethylethyl)oxy]carbonyl}-3-methyl-1-piperazinyl)methyl]phenyl}acetic Acid (D59)

[4-(Bromomethyl)phenyl]acetic acid (75 g, 0.33 mol) was added to 4-methyl-2-pentanone (MIBK, 750 ml), cooled to 7° C. and the chiral piperazine (1,1-dimethylethyl (2S)-2-methyl-1-piperazinecarboxylate, 72 g, 0.36 mol) added in one portion. The slurry was cooled to 5° C. and diisopropylethylamine (DIPEA, 112 ml, 0.64 mol) added drop-wise over 21 min keeping the temperature below 5° C. Following this addition, the slurry was stirred at 3° C. overnight. Sodium hydroxide (1M, 750 ml) was added, the reaction mixture adjusted to 21° C. and the layers allowed to separate. The reaction vessel was washed with water (250 ml) and the aqueous layer returned to the reaction vessel. Fresh MIBK (375 ml) was added and the mixture stirred the mixture was acidified to about pH 5 by addition of concentrated hydrochloric acid. The contents of the vessel were stirred vigorously for 5 min, the phases were separated and the aqueous extracted with more MIBK (2×375 ml) adjusting the pH of the aqueous layer to 5.1-5.3 each time. The organic phases were combined (approx 1.5 liters) and 500 ml of solvent removed. The reaction mixture was then cooled to room temperature overnight and an additional 500 ml of solvent removed to leave a final volume of 600 ml (8 vol) giving a dry solution of the title product.

Description 60

1,1-Dimethylethyl (2S)-4-{[4-(2-{4-[(3-fluorophenyl)amino]-1-piperidinyl}-2-oxoethyl)phenyl]methyl}-2-methyl-1-piperazinecarboxylate Carbonyldiimidazole (CDI, 53 g, 0.33 mol) was added to the dry solution from D59 (cooled to room temperature) in two portions with 15 min after each addition. The resulting mixture was warmed to 62° C. and stirred for 15 min. D58 (63.5 g, 0.33 mol) was added in one portion causing a minor exothermic reaction warming the contents to 68° C. The mixture was cooled to 62° C. and stirred for 2 h then cooled to 0° C. over 2 hr and held at 0° C. overnight. The final slurry was filtered, the solids washed with ice-cold MIBK (3×75 ml), dried in vacuo at 50° C. overnight to give the title product (142 g). $\delta_H$ (CDCl$_3$, 500 MHz) 1.08 (1H, m), 1.23 (3H, d), 1.35 (1H, m), 1.45 (9H, s), 1.95 (1H, m), 2.05 (2H, m), 2.10 (1H, m), 2.57 (1H, d), 2.73 (1H, d), 2.89 (1H, m), 3.10 (2H, m), 3.37 (1H, d), 3.40 (1H, m), 3.50 (1H, d), 3.60 (1H, br s), 3.73 (2H, s), 3.77 (1H, m), 3.85 (1H, m), 4.15 (1H, m), 4.51 (1H, m), 6.24 (1H, m), 6.31 (1H, m), 6.38 (1H, m), 7.06 (1H, m), 7.19 (2H, m), 7.27 (2H, m).

EXAMPLE 1

1-[(4-{[(3R,5S)-3,5-Dimethyl-1-piperazinyl]methyl}phenyl)acetyl]-N-(4-fluorophenyl)-4-piperidinamine (E1)

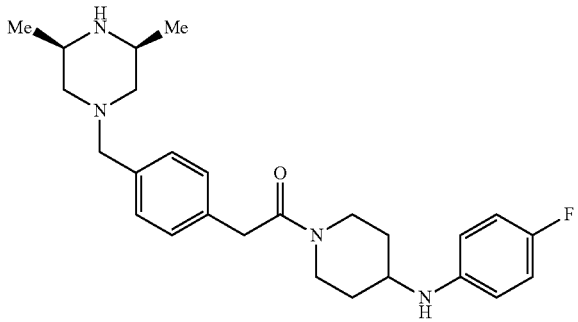 [SMILES: C[C@@H]1CN(Cc2ccc(CC(=O)N3CCC(Nc4ccc(F)cc4)CC3)cc2)C[C@H](C)N1]

A mixture of D4 (149 mg, 0.438 mmol) and 1,1-dimethylethyl (2R,6S)-2,6-dimethyl-1-piperazinecarboxylate (94 mg, 0.438 mmol) in 1,2-DCE (3 ml) was stirred for 5 mins at room temperature. Sodium tri(acetoxy)borohydride (139 mg, 0.66 mmol) was added and the mixture was stirred for 3 h then saturated aq. NaHCO$_3$ solution was added. The mixture was stirred for 15 mins then extracted with EtOAc. The combined extracts were dried (Na$_2$SO$_4$) and concentrated in vacuo to give the crude product which was purified by chromatography. Elution with 20-90% EtOAc/pentane gave 1,1-dimethylethyl (2R,6S)-4-{[4-(2-{4-[(4-fluorophenyl)amino]-1-piperidinyl}-2-oxoethyl)phenyl]methyl}-2,6-dimethyl-1-piperazinecarboxylate (143 mg). $\delta_H$ (CDCl$_3$, 400 MHz) 1.06 (1H, m), 1.27 (6H, d), 1.30 (1H, m), 1.46 (9H, s), 1.93 (1H, m), 2.05 (1H, m), 2.12 (2H, dd), 2.59 (2H, d), 2.88 (1H, m), 3.13 (1H, m), 3.29 (1H, m), 3.38 (1H, m), 3.45 (2H, s), 3.74 (2H, s), 3.86 (1H, m), 4.07 (2H, m), 4.50 (1H, m), 6.50 (2H, m), 6.87 (2H, t), 7.20 (2H, m), 7.31 (2H, d). MS (ES): MH$^+$ 539

This whole was dissolved in 2:1 DCM/TFA and stirred for 1 h. The mixture was concentrated and the free base title compound was isolated using an Isolute SCX cartridge. $\delta_H$ (CDCl$_3$, 400 MHz) 1.01 (6H, d), 1.06 (1H, m), 1.29 (1H, m), 1.62 (2H, t), 1.93 (1H, m), 2.04 (1H, m), 2.74 (2H, d), 2.83-2.94 (3H, m), 3.12 (1H, m), 3.36 (2H, m), 3.46 (2H, s), 3.73 (2H, s), 3.86 (1H, m), 4.51 (1H, m), 6.55 (2H, m), 6.86 (2H, t), 7.20 (2H, m), 7.26 (2H, d). MS (ES): MH$^+$ 439

This whole was converted to the dihydrochloride salt of the title compound (104 mg).

EXAMPLE 2

N-(3-Fluorophenyl)-1-[(4-{[(3S)-3-methyl-1-piperazinyl]methyl}phenyl)acetyl]-4-piperidinamine (E2)

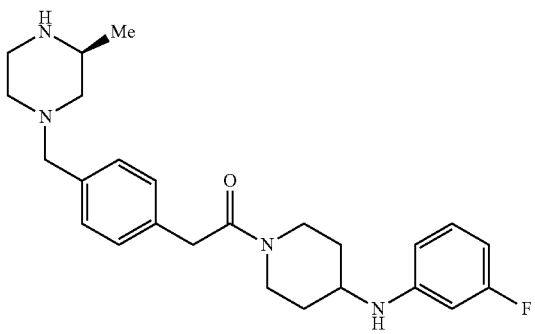 [SMILES: C[C@H]1CN(Cc2ccc(CC(=O)N3CCC(Nc4cccc(F)c4)CC3)cc2)CCN1]

A mixture of D8 (115 mg, 0.3 mmol), polymer-supported DCC (270 mg, 1.7 mmol/g, 0.45 mmol) and 1-hydroxybenzotriazole (55 mg, 0.36 mmol) in 2:1 DMF/DCM (3 ml) was treated with D5b (58 mg, 0.3 mmol) and stirred overnight. Scavenger resins (PS-trisamine, PS-isocyanate and Si-carbonate) together with DCM (~3 ml) were added. The mixture was stirred for ~2 h and then filtered and concentrated. Chromatography (0-60% EtOAc/pentane) gave phenylmethyl (2S)-4-{[4-(2-{4-[(3-fluorophenyl)amino]-1-piperidinyl}-2-oxoethyl)phenyl]methyl}-2-methyl-1-piperazinecarboxylate (81.6 mg). MS (ES): MH$^+$ 559

This whole was hydrogenated in MeOH (~5 ml) with 10% Pd/C catalyst (~20 mg) for 2 h. Chromatography (0-20% MeOH/DCM) gave the title compound (29.6 mg). $\delta_H$ (CDCl$_3$, 400 MHz) 7.26 (2H, d), 7.20 (2H, m), 7.06 (1H, q), 6.36 (1H, m), 6.31 (1H, m), 6.25 (1H, m), 4.52 (1H, m), 3.86 (1H, m), 3.73 (2H, s), 3.66 (1H, m), 3.48 (2H, s), 3.41 (1H, m), 2.84-3.16 (6H, m), 2.76 (2H, m), 2.03-2.13 (2H, m), 1.94 (1H, m), 1.78 (1H, t), 1.34 (1H, m), 1.05 (4H, m). MS (ES): MH$^+$ 425

This whole was treated with 1.1 eq of 1M HCl in Et$_2$O to give a hydrochloride salt of the title compound (25 mg). MS (ES): MH$^+$ 425

EXAMPLE 2

Alternative Method (A)

N-(3-fluorophenyl)-1-[(4-{[(3S)-3-methyl-1-piperazinyl]methyl}phenyl)acetyl]-4-piperidinamine (E2)

A solution of D19 (83.01 g, 0.158 mol) in DCM (900 ml) was split into two portions and each cooled to 0° C. and treated with TFA (100 ml). After stirring for 0.5 h at 0° C. the reactions were warmed to room temperature and stirred for 3.25 h. The solvent was removed in vacuo and the residues combined and partitioned between DCM and 2M NaOH solution. The aqueous phase was re-extracted with DCM (×2) and the combined organics were then washed with 2M NaOH and brine. The organics were dried and concentrated in vacuo to give an off-white solid. The NaOH phase was re-extracted with DCM, which was dried and concentrated to give a further batch of white foam. The two batches were combined to give the title compound as an off-white solid (66.94 g). MS (ES): MH$^+$ 425.

This material (66.229, 0.156 mmol) was dissolved in EtOAc (1.71) at 45-50° C. to give an homogenous pale yellow solution which was then cooled to room temperature and flushed with argon. 1M HCl in Et$_2$O (156 ml, 0.156M) was added with vigorous stirring and after a further 15 mins, the resultant creamy-white precipitate was collected by filtration under a blanket of argon. This was washed with further EtOAc (0.81) and partially dried on the filter under a blanket of argon for 15 mins. The solid was further dried at 80° C. in vacuo to give the hydrochloride salt of the title compound (58.95 g). MS (ES): MH$^+$ 425.

EXAMPLE 2

Alternative Method (B)

N-(3-fluorophenyl)-1-[(4-{[(3S)-3-methyl-1-piperazinyl]methyl}phenyl)acetyl]-4-piperidinamine (E2)

A mixture of D60 (20 g, 0.038 mol) and 1M Sulfuric acid (80 ml, 4 vol) was heated to 55° C.±3° C. and the slurry stirred for 90 min. The solution was cooled to 25° C. and extracted with i-PrOAc (100 ml, 5 vol). The sulphuric acid solution was diluted with fresh i-PrOAc (100 ml, 5 vol) and the mixture basified to pH 12-14 by slow addition of 32% w/w sodium hydroxide (23 g, 1.15 wt), keeping the temperature between 20° C. and 30° C. The aqueous layer was separated, extracted twice more with i-PrOAc (2×100 ml) and the combined organic extracts washed with 20% w/v aqueous NaCl (60 ml, 3 vol).

The organic solution was distilled down at atmospheric pressure to a final volume of 200 ml and diluted with fresh i-PrOAc (100 ml, 5 vol). The solution was heated to reflux, filtered hot through a filter paper and distilled down at atmospheric pressure to a final volume of 200 ml. The solution was then cooled slowly over 1 h to 30° C. and the resulting slurry was cooled to 5° C. and stirred for 45 min. The solid was collected by filtration, washed with chilled i-PrOAc (2×2 vol) and dried in vacuo overnight to give the title product (12.63 g). $\delta_H$ (CDCl$_3$, 400 MHz) 7.27 (2H, d), 7.20 (2H, m), 7.06 (1H, q), 6.37 (1H, m), 6.32 (1H, m), 6.25 (1H, m), 4.52 (1H, m), 3.86 (1H, m), 3.74 (2H, s), 3.61 (1H, m), 3.46 (2H, s), 3.41 (1H, m), 3.12 (1H, m), 2.81-2.94 (4H, m), 2.73 (2H, m), 1.92-2.06 (3H, m), 1.65 (1H, m), 1.30 (1H, m), 1.07 (1H, m), 0.99 (3H, d).

The following examples, E3-E11, were prepared from D8 and the amines indicated in the table using methods similar to that described for Example 2, although MP-carbonate was used in place of Si-carbonate in the amide formation step and palladium black was used in place of 10% Pd/C in the deprotection step.

Compounds possess the general structure:

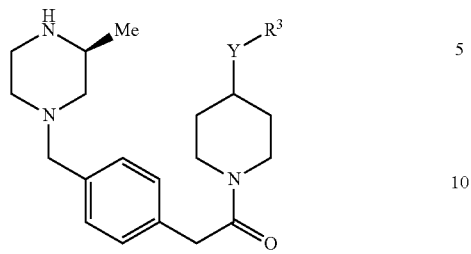

Where YR³ is exemplified in the table below

| Example | Amine Precursor | Compound | YR³ | MH⁺ |
|---|---|---|---|---|
| 3 | D2 | N-(4-Fluorophenyl)-1-[(4-{[(3S)-3-methyl-1-piperazinyl]methyl}-phenyl)acetyl]-4-piperidinamine (E3) | | 425 |
| 4 | D10b | 3-({1-[(4-{[(3S)-3-Methyl-1-piperazinyl]methyl}phenyl)acetyl]-4-piperidinyl}amino)benzonitrile (E4) | | 432 |
| 5 | D11b | 4-({1-[(4-{[(3S)-3-Methyl-1-piperazinyl]methyl}phenyl)acetyl]-4-piperidinyl}amino)benzonitrile (E5) | | 432 |
| 6 | D9b | N-(3,4-Difluorophenyl)-1-[(4-{[(3S)-3-methyl-1-piperazinyl]methyl}-phenyl)acetyl]-4-piperidinamine (E6) | | 443 |
| 7 | D12b | N-[4-Fluoro-3-(methyloxy)phenyl]-1-[(4-{[(3S)-3-methyl-1-piperazinyl]methyl}phenyl)acetyl]-4-piperidinamine (E7) | | 455 |
| 8 | D15 | (3S)-1-{[4-(2-{4-[(4-Fluorophenyl)oxy]-1-piperidinyl}-2-oxoethyl)phenyl]methyl}-3-methylpiperazine (E8) | | 426 |
| 9 | D14 | (3S)-1-{[4-(2-{4-[(3-Fluorophenyl)oxy]-1-piperidinyl}-2-oxoethyl)phenyl]methyl}-3-methylpiperazine (E9) | | 426 |
| 10 | D21 | 1-[(4-{[(3S)-3-Methyl-1-piperazinyl]methyl}phenyl)acetyl]-N-[3-(trifluoromethyl)phenyl]-4-piperidinamine (E10) | | 475 |
| 11 | D23 | 1-[(4-{[(3S)-3-Methyl-1-piperazinyl]methyl}phenyl)acetyl]-N-[4-(trifluoromethyl)phenyl]-4-piperidinamine (E11) | | 475 |

The following example, E12, was prepared from D26 and the amine indicated in the table using a method similar to that described for Example 2, although MP-carbonate was used in place of Si-carbonate in the amide formation step and palladium black was used in place of 10% Pd/C in the deprotection step.

Compounds possess the general structure:

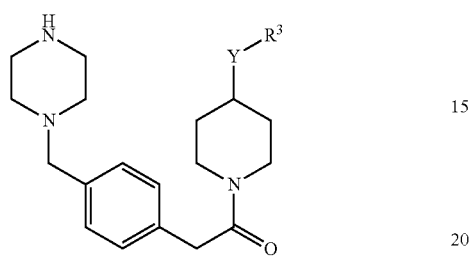

Where YR³ is exemplified in the table below

| Example | Amine Precursor | Compound | YR³ | MH⁺ |
|---|---|---|---|---|
| 12 | D5B | N-(3-Fluorophenyl)-1-{[4-(1-piperazinylmethyl)phenyl]acetyl}-4-piperidinamine (E12) | | 411 |

EXAMPLE 13

N-(3-Fluorophenyl)-1-[(4-{[(3R)-3-methyl-1-piperazinyl]methyl}phenyl)acetyl]-4-piperidinamine (E13)

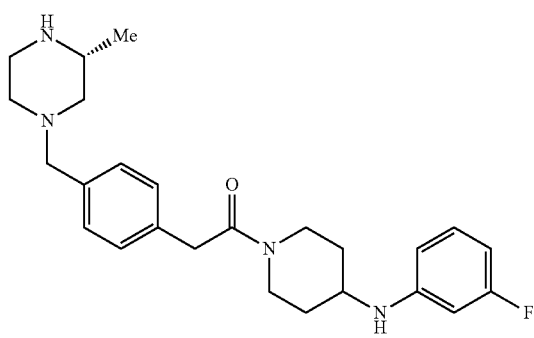 [SMILES: C[C@@H]1CN(Cc2ccc(CC(=O)N3CCC(Nc4cccc(F)c4)CC3)cc2)CCN1]

A solution of D29 (136 mg, 0.24 mmol) was hydrogenated in MeOH (5 ml) with palladium black catalyst (68 mg) for 0.75 h. The reaction mixture was concentrated in vacuo to give a pale yellow crude oil which was purified by chromatography. Elution with 0-10% (2M $NH_3$ in MeOH)/DCM gave the title compound as a colourless oil (38 mg). $\delta_H$ (CDCl₃, 400 MHz) 7.27 (2H, d), 7.20 (2H, d), 7.07 (1H, q), 6.37 (1H, m), 6.31 (1H, m), 6.25 (1H, d), 4.52 (1H, m), 3.86 (1H, m), 3.74 (2H, s), 3.62 (1H, m), 3.47 (2H, s), 3.42 (1H, m), 3.13 (1H, m), 2.90 (4H, m), 2.75 (2H, m), 2.00 (4H, m), 1.69 (1H, t), 1.30 (1H, m), 1.06 (1H, m), 1.02 (3H, d). MS (ES): MH⁺ 425.

This whole was treated with 1.1 eq of 1M HCl in Et₂O to give a hydrochloride salt of the title compound (41 mg). MS (ES): MH⁺ 425.

The following examples, E14-E20, were prepared from D28 and the amines indicated in the table using methods similar to that described for Example 2, although MP-carbonate was used in place of Si-carbonate in the amide formation step and palladium black was used in place of 10% Pd/C in the deprotection step.

Compounds possess the general structure:

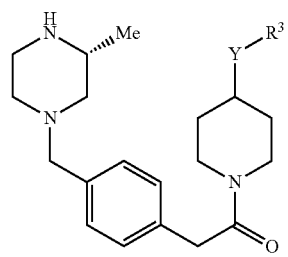

Where YR³ is exemplified in the table below

| Example | Amine Precursor | Compound | YR³ | MH⁺ |
|---|---|---|---|---|
| 14 | D9b | N-(3,4-Difluorophenyl)-1-[(4-{[(3R)-3-methyl-1-piperazinyl]methyl}phenyl)acetyl]-4-piperidinamine (E14) | 3,4-difluorophenyl-NH- | 443 |
| 15 | D15 | (3R)-1-{[4-(2-{4-[(4-Fluorophenyl)oxy]-1-piperidinyl}-2-oxoethyl)phenyl]methyl}-3-methylpiperazine (E15) | 4-fluorophenyl-O- | 426 |
| 16 | D14 | (3R)-1-{[4-(2-{4-[(3-Fluorophenyl)oxy]-1-piperidinyl}-2-oxoethyl)phenyl]methyl}-3-methylpiperazine (E16) | 3-fluorophenyl-O- | 426 |
| 17 | D31 | 4-({1-[(4-{[(3R)-3-Methyl-1-piperazinyl]methyl}phenyl)acetyl]-4-piperidinyl}oxy)benzonitrile (E17) | 4-cyanophenyl-O- | 433 |
| 18 | D11b | 4-({1-[(4-{[(3R)-3-Methyl-1-piperazinyl]methyl}phenyl)acetyl]-4-piperidinyl}amino)benzonitrile (E18) | 4-cyanophenyl-NH- | 432 |
| 19 | D10b | 3-({1-[(4-{[(3R)-3-Methyl-1-piperazinyl]methyl}phenyl)acetyl]-4-piperidinyl}amino)benzonitrile (E19) | 3-cyanophenyl-NH- | 432 |
| 20 | D21 | 1-[(4-{[(3R)-3-Methyl-1-piperazinyl]methyl}phenyl)acetyl]-N-[3-(trifluoromethyl)phenyl]-4-piperidinamine (E20) | 3-trifluoromethylphenyl-NH- | 475 |

EXAMPLE 21

N-(3-Fluorophenyl)-1-[(3-(methyloxy)-4-{[(3S)-3-methyl-1-piperazinyl]methyl}phenyl)acetyl]-4-piperidinamine (E21)

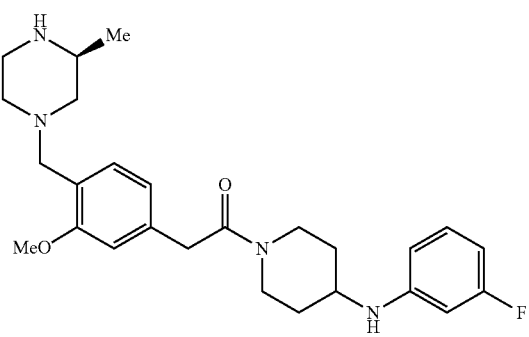 [SMILES: COc1cc(CC(=O)N2CCC(Nc3cccc(F)c3)CC2)ccc1CN1CCN[C@@H](C)C1]

A solution of D37 (42 mg, 0.075 mmol) in DCM (5 ml) was treated with TFA (1.3 ml) and the reaction was stirred at room temperature under argon. The solvent was removed in vacuo and the residue partitioned between DCM and water. The aqueous was basified to pH14 with 2M NaOH solution then extracted with EtOAc (×3). The combined organics were dried and concentrated in vacuo to give the title compound as a colourless oil (20 mg). $\delta_H$ (CDCl$_3$, 250 MHz) 7.27 (1H, d), 7.07 (1H, q), 6.79 (2H, m), 6.22-6.41 (3H, m), 4.52 (1H, m), 3.87 (1H, m), 3.81 (3H, s), 3.74 (2H, s), 3.65 (1H, m), 3.54 (2H, s), 3.40 (1H, m), 3.14 (1H, m), 2.79-2.97 (6H, m), 1.92-2.22 (4H, m), 1.77 (1H, m), 1.27 (1H, m), 1.07 (1H, m), 1.02 (3H, d). MS (ES): MH⁺ 455.

This whole was treated with 1M HCl in Et$_2$O (40 ul) to give a hydrochloride salt of the title compound as a cream solid (14 mg). MS (ES): MH⁺ 455.

EXAMPLE 22

2-Fluoro-5-({1-[(4-{[(3S)-3-methyl-1-piperazinyl]methyl}phenyl)acetyl]-4-piperidinyl}amino)benzonitrile (E22)

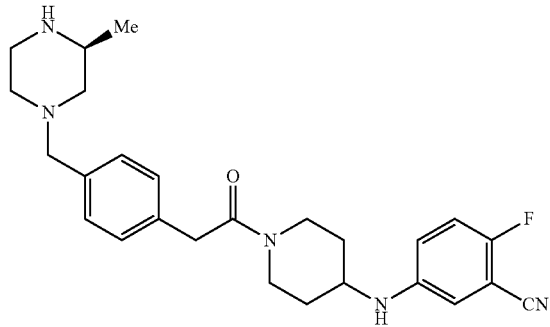 [SMILES: C[C@H]1CN(Cc2ccc(CC(=O)N3CCC(Nc4ccc(F)c(C#N)c4)CC3)cc2)CCN1]

To a solution of D40 (133 mg, 0.24 mmol) in DCM (4 ml) cooled in an ice bath was added TFA (1 ml). The mixture was stirred for 1 h then warmed to room temperature and stirred for 2 h. The solvent was removed in vacuo and purification by chromatography eluting with 0-10% (2M $NH_3$ in MeOH)/DCM followed MDAP gave the title compound as a clear solid (58.5 mg). $\delta_H$ (CDCl$_3$, 400 MHz) 7.31 (2H, d), 7.21 (2H, d), 7.07 (2H, m), 7.00 (1H, m), 5.38 (1H, d), 3.94 (1H, m), 3.55 (2H, s), 3.49 (4H, m), 2.81-2.98 (5H, m), 2.75 (2H, m), 2.02 (3H, m), 1.69 (1H, t), 1.46 (2H, m), 1.00 (3H, d). MS (ES): MH+ 450.

This whole was dissolved in DCM and treated with 1M HCl in Et$_2$O (143 ul) to give a hydrochloride salt of the title compound (75 mg). MS (ES): MH+ 450.

EXAMPLE 23

1-[3-(4-{[(3R,5S)-3,5-Dimethyl-1-piperazinyl]methyl}phenyl)propanoyl]-N-(4-fluorophenyl)-4-piperidinamine (E23)

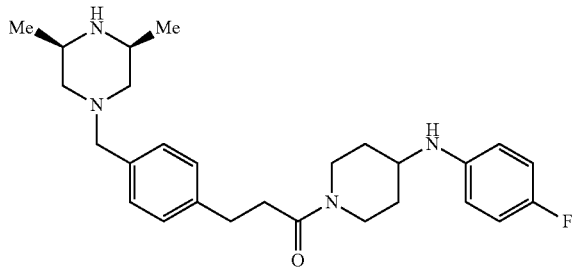 [SMILES: C[C@@H]1CN(Cc2ccc(CCC(=O)N3CCC(Nc4ccc(F)cc4)CC3)cc2)C[C@H](C)N1]

To a mixture of D41 (100 mg, 0.282 mmol) and 1,1-dimethylethyl (2R,6S)-2,6-dimethyl-1-piperazinecarboxylate (61 mg, 0.283 mmol) in 1,2-DCE (5 ml) was added sodium tri(acetoxy)borohydride (90 mg, 0.423 mmol) and the mixture stirred at room temperature overnight. Saturated aq. NaHCO$_3$ solution was added, the mixture was stirred for 15 mins and then extracted with EtOAc. The combined extracts were dried (Na$_2$SO$_4$) and concentrated in vacuo to give the crude product which was purified by chromatography eluting with 0-100% EtOAc/pentane to give 1,1-dimethylethyl (2R,6S)-4-{[4-(3-{4-[(4-fluorophenyl)amino]-1-piperidinyl}-3-oxopropyl)phenyl]methyl}-2,6-dimethyl-1-piperazinecarboxylate. MS (ES): MH+ 553

This whole was dissolved in 2:1 DCM/TFA (3 ml) and stirred for 1.5 h. The mixture was concentrated and the title compound (100 mg) was isolated using an Isolute SCX cartridge. $\delta_H$ (CDCl$_3$, 400 MHz) 7.23 (2H, d), 7.17 (2H, d), 6.88 (2H, t), 6.53 (2H, m), 4.52 (1H, m), 3.79 (1H, m), 3.42 (4H, m), 3.09 (1H, m), 2.94 (4H, m), 2.83 (1H, m), 2.75 (2H, m), 2.63 (2H, m), 2.03 (2H, m), 1.59 (2H, t), 1.29 (1H, m), 1.17 (1H, m), 1.02 (6H, d). MS (ES): MH+ 453.

This whole was dissolved in DCM and treated with 1M HCl in Et$_2$O (243 ul) to give hydrochloride salt of the title compound (98 mg). MS (ES): MH+ 453.

The following example, E24, was prepared from D42 using a method similar to that described for Example 23.

Compounds possess the general structure:

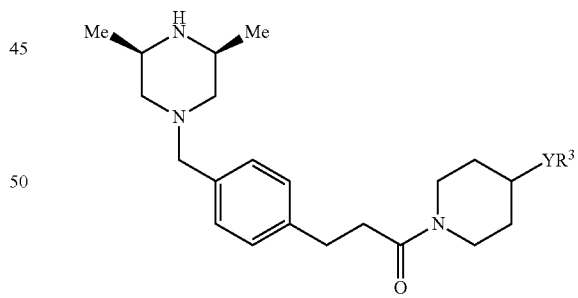

Where YR$^3$ is exemplified in the table below

| Example | Compound | YR$^3$ | MH+ |
|---|---|---|---|
| 24 | 1-[3-(4-{[(3R,5S)-3,5-Dimethyl-1-piperazinyl]methyl}phenyl)propanoyl]-N-(3-fluorophenyl)-4-piperidinamine (E24) | (3-fluorophenylamino) | 453 |

EXAMPLE 25

N-(4-Fluorophenyl)-1-[3-(4-{[(3S)-3-methyl-1-piperazinyl]methyl}phenyl)propanoyl]-4-piperidinamine (E25)

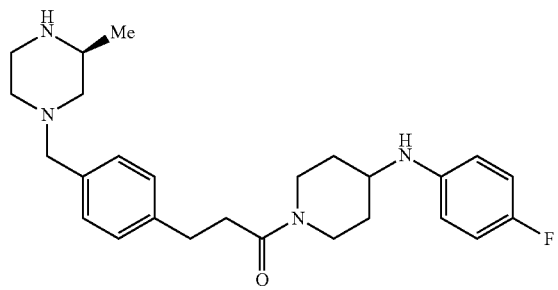 [SMILES: C[C@H]1CN(Cc2ccc(CCC(=O)N3CCC(Nc4ccc(F)cc4)CC3)cc2)CCN1]

To a mixture of D41 (100 mg, 0.282 mmol) and phenylmethyl (2S)-2-methyl-1-piperazinecarboxylate (66 mg, 0.281 mmol) in 1,2-DCE (5 ml) was added sodium tri(acetoxy)borohydride (90 mg, 0.423 mmol) and the mixture stirred at room temperature overnight. Saturated aq. NaHCO$_3$ solution was added, the mixture was stirred for 15 mins and then extracted with EtOAc. The combined extracts were dried (Na$_2$SO$_4$) and concentrated in vacuo to give the crude product which was purified by chromatography eluting with 0-100% EtOAc/pentane to give phenylmethyl (2S)-4-{[4-(3-{4-[(4-fluorophenyl)amino]-1-piperidinyl}-3-oxopropyl)phenyl]methyl}-2-methyl-1-piperazinecarboxylate. MS (ES): MH$^+$ 572

This whole was hydrogenated in MeOH (5 ml) with 10% Pd/C catalyst (20 mg) for 2.5 h. The mixture was filtered, concentrated and purified by MDAP to give the title compound (69 mg). δ$_H$(CDCl$_3$, 400 MHz) 7.24 (2H, d), 7.17 (2H, s), 6.88 (2H, t), 6.53 (2H, m), 4.51 (1H, m), 3.79 (1H, m), 3.43 (4H, m), 3.09 (1H, m), 2.73-2.98 (8H, m), 2.63 (2H, t), 1.96-2.06 (5H, m), 1.27 (1H, m), 1.15 (1H, m), 1.00 (3H, d). MS (ES): MH$^+$ 439.

This whole was treated with 1M HCl in Et$_2$O (174 ul) to give a hydrochloride salt of the title compound (69 mg). MS (ES): MH$^+$ 439.

The following example, E26, was prepared from D42 using a method similar to that described for Example 25.

Compounds possess the general structure:

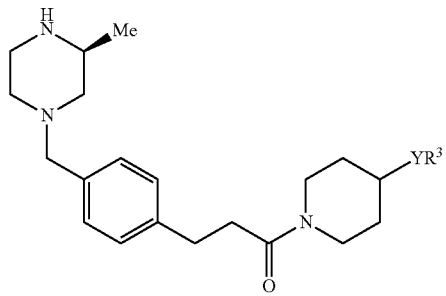

Where YR$^3$ is exemplified in the table below

EXAMPLE 27

1-[2-(4-{[(3R,5S)-3,5-Dimethyl-1-piperazinyl]methyl}phenyl)propanoyl]-N-(4-fluorophenyl)-4-piperidinamine (E27)

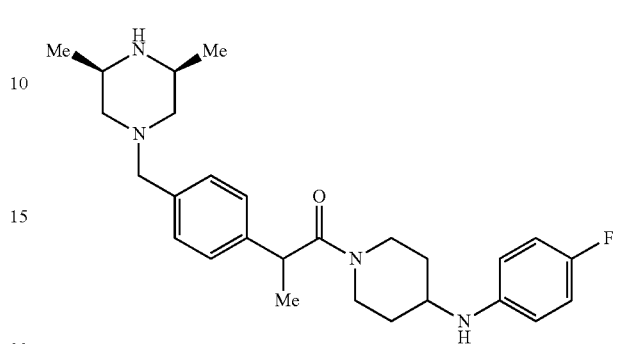

A mixture of D46 (100 mg, 0.27 mmol), polymer-supported DCC (310 mg, 1.3 mmol/g, 0.40 mmol) and 1-hydroxybenzotriazole (50 mg, 0.324 mmol) in 2:1 DMF/DCM (3 ml) was treated with D2 (51 mg, 0.26 mmol) and the mixture stirred overnight. Scavenger resins (PS-trisamine, PS-isocyanate and Si-carbonate) together with DCM (~3 ml) were added. The mixture was stirred for ~3 h and then filtered and concentrated to give 1,1-dimethylethyl (2R,6S)-4-{[4-(2-{4-[(4-fluorophenyl)amino]-1-piperidinyl}-1-methyl-2-oxoethyl)phenyl]methyl}-2,6-dimethyl-1-piperazinecarboxylate. MS (ES): MH$^+$ 553. This whole was dissolved in DCM (2 ml) and TFA (1 ml) then stirred for 1.5 h. The solvents were removed in vacuo and the residue re-evaporated from toluene and ether. Purification using an Isolute SCX cartridge eluting with MeOH followed by 2M NH$_3$ in MeOH gave the title compound. MS (ES): MH$^+$ 453. This whole was dissolved in DCM and treated with 1.1 eq 1M HCl in ether to give a hydrochloride salt of the title compound (122 mg). MS (ES): MH$^+$ 453.

The following example, E28, was prepared from D46 and D5b using a method similar to that described for Example 27.

Compounds possess the general structure:

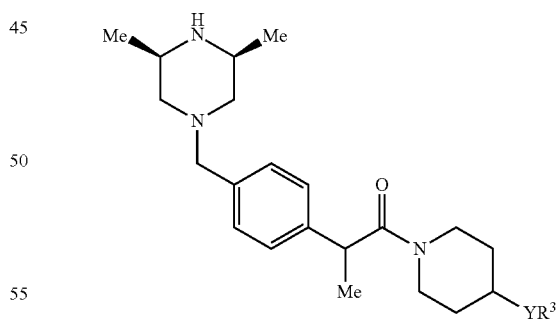

| Example | Compound | YR$^3$ | MH$^+$ |
|---|---|---|---|
| 26 | N-(3-Fluorophenyl)-1-[3-(4-{[(3S)-3-methyl-1-piperazinyl]methyl}phenyl)propanoyl]-4-piperidinamine (E26) | ![3-fluorophenylamino] | 439 |

Where YR³ is exemplified in the table below

| Example | Compound | YR³ | MH⁺ |
|---|---|---|---|
| 28 | 1-[2-(4-{[(3R,5S)-3,5-Dimethyl-1-piperazinyl]methyl}phenyl)propanoyl]-N-(3-fluorophenyl)-4-piperidinamine (E28) | 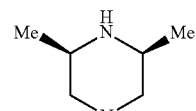 | 453 |

EXAMPLE 29

1-[2-(4-{[(3R,5S)-3,5-Dimethyl-1-piperazinyl]methyl}phenyl)-2-methylpropanoyl]-N-(4-fluorophenyl)-4-piperidinamine (E29)

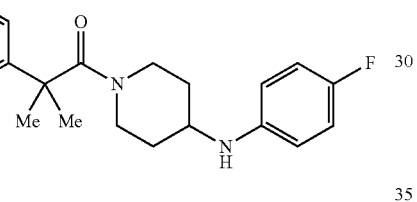

A mixture of D48 (100 mg, 0.256 mmol), polymer-supported DCC (296 mg, 1.3 mmol/g, 0.385 mmol) and 1-hydroxybenzotriazole (18 mg, 0.128 mmol) in 1:4 DMF/DCM (5 ml) was treated with D2 (50 mg, 0.256 mmol) and the mixture stirred overnight. Scavenger resins (PS-trisamine, PS-isocyanate and Si-carbonate) were added, the mixture was shaken for 2 h and then filtered and concentrated to give 1,1-dimethylethyl (2R,6S)-4-{[4-(2-{4-[(4-fluorophenyl)amino]-1-piperidinyl}-1,1-dimethyl-2-oxoethyl)phenyl]methyl}-2,6-dimethyl-1-piperazinecarboxylate, MS (ES): MH⁺ 567. This whole was treated with 4M HCl in 1,4-dioxane (2 ml) for 1 h. The solvents were removed in vacuo to give the dihydrochloride salt of the title compound (115 mg). MS (ES): MH⁺ 467.

The following examples, E30-E31, were prepared from D48 and the amine precursor indicated in the table using methods similar to that described in Example 29.

Compounds possess the general structure:

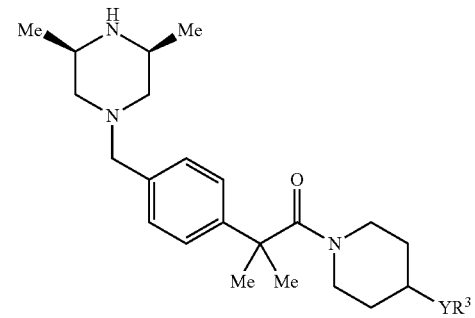

Where YR³ is exemplified in the table below

| Example | Amine Precursor | Compound | YR³ | MH⁺ |
|---|---|---|---|---|
| 30 | D5b | 1-[2-(4-{[(3R,5S)-3,5-Dimethyl-1-piperazinyl]methyl}phenyl)-2-methylpropanoyl]-N-(3-fluorophenyl)-4-piperidinamine (E30) |  | 467 |
| 31 | D15 | (3R,5S)-1-{[4-(2-{4-[(4-Fluorophenyl)oxy]-1-piperidinyl}-1,1-dimethyl-2-oxoethyl)phenyl]methyl}-3,5-dimethylpiperazine (E31) |  | 468 |

EXAMPLE 32

N-(3-Fluorophenyl)-1-[3-(5-{[(3S)-3-methyl-1-piperazinyl]methyl}-2-pyridinyl)propanoyl]-4-piperidinamine (E32)

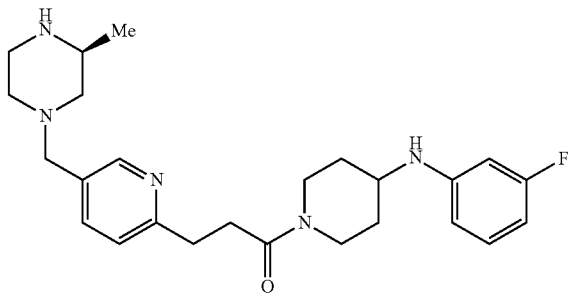 [SMILES: C[C@H]1CN(Cc2ccc(CCC(=O)N3CCC(Nc4cccc(F)c4)CC3)nc2)CCN1]

A solution of D52 (47 mg, 0.082 mmol) was hydrogenated in MeOH (4 ml) with palladium black catalyst (23 mg) for 1.5 h. The reaction mixture was worked up and purified by chromatography to give the title compound (4 mg). $\delta_H$ (CDCl$_3$, 400 MHz) 8.42 (1H, d), 7.57 (1H, dd), 7.20 (1H, d), 7.08 (1H, q), 6.26-6.41 (3H, m), 4.50 (1H, m), 3.92 (1H, m), 3.67 (1H, m), 3.46 (2H, m), 3.15 (3H, m), 2.81-2.98 (6H, m), 2.73 (2H, d), 2.05 (3H, m), 1.67 (2H, m), 1.39 (2H, m), 1.06 (1H, m), 1.02 (3H, d). MS (ES): MH$^+$ 440.

This whole was converted to a hydrochloride salt of the title compound (4 mg).

EXAMPLE 33

1-[(3-Chloro-4-{[(3S)-3-methyl-1-piperazinyl]methyl}phenyl)acetyl]-N-(3-fluorophenyl)-4-piperidinamine (E33)

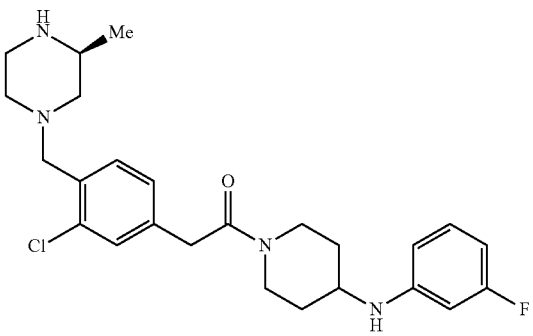 [SMILES: C[C@H]1CN(Cc2ccc(CC(=O)N3CCC(Nc4cccc(F)c4)CC3)cc2Cl)CCN1]

To a solution of D55 (156 mg, 0.28 mmol) in DCM (20 ml) was added TFA (5 ml). The mixture was stirred for at room temperature for 6 h. The solvent was removed in vacuo and the residue partitioned between DCM and water. The aqueous layer was basified to pH14 with concentrated NaOH solution then extracted with DCM (×3). The combined organics were dried (MgSO$_4$) and concentrated to give the title compound as a colourless oil (118 mg). $\delta_H$ (CDCl$_3$, 400 MHz) 7.43 (1H, d), 7.25 (1H, s), 7.09 (2H, m), 6.38 (1H, td), 6.33 (1H, dd), 6.26 (1H, m), 4.52 (1H, m), 3.85 (1H, m), 3.70 (2H, s), 3.62 (1H, m), 3.57 (2H, s), 3.44 (1H, m), 3.16 (1H, m), 2.91 (4H, m), 2.77 (2H, m), 2.07 (3H, m), 1.78 (1H, t), 1.33 (1H, m), 1.15 (1H, m), 1.02 (3H, d). MS (ES): MH$^+$ 459/461

This whole was dissolved in MeOH and treated with 1M HCl in Et$_2$O (0.28 ml) to give a hydrochloride salt of the title compound (106 mg). MS (ES): MH$^+$ 459/461.

GPR38 FLIPR Functional Agonist Assay Protocol 24 hours prior to assay, CHO-K1 cells stably expressing the GPR38 receptor were seeded (10,000 cells/well) into poly-D-lysine coated 384-well black-wall, clear-bottom microtitre plates (Greiner). On the day of assay, media was aspirated from cell plates using a cell washer (leaving 10 ul of media). Cells were immediately loaded with loading buffer [Tyrodes (Elga water+145 mM NaCl+5 mM KCl+20 mM HEPES+10 mM glucose+1 mM MgCl$_2$)+1.5 mM CaCl$_2$+ 0.714 mg/ml Probenicid (predissolved in 1 M NaOH)+0.25 mM brilliant black+2 uM Fluo 4 dye], and incubated at 37.5° C. for 1 hour.

Plates were then assayed on a FLuorometric Imaging Plate Reader (FLIPR, Molecular Devices).

Master compound plates were prepared in 100% DMSO. A top concentration of 3 mM was used (giving 12 μM final concentration in assay) and this was serially diluted 1 in 4. 1 ul from the master plate was transferred to a daughter plate, to which 50 μl of compound dilution buffer (Tyrodes+1 mg/ml BSA+1.5 mM CaCl$_2$) was added. In the FLIPR, 10 ul of test compound was added to the cells and changes in fluorescence measured over a 1 minute timeframe. Maximum change in fluorescence over baseline was used to determine agonist response and concentration response curves were constructed, using a 4-parameter logistic equation.

Exemplified compounds of the invention have a pEC50>6.5 in the FLIPR assay,

What is claimed is:

1. A compound which is N-(3-Fluorophenyl)-1-[(4-{[(3S)-3-methyl-1-piperazinyl]methyl}phenyl)acetyl]-4-piperidinamine having the formula:

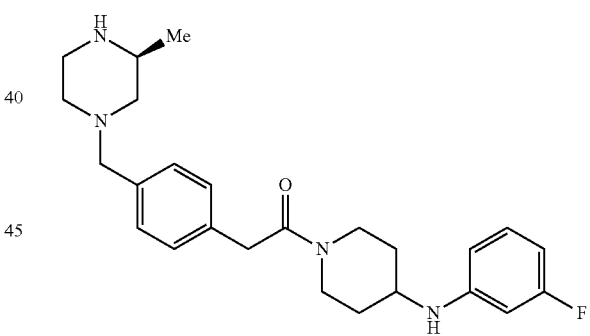

or a pharmaceutically acceptable salt thereof.

2. A pharmaceutical composition comprising the compound or salt according to claim 1.

3. A method of treatment for a condition or disorder which is mediated via GPR-38 receptors in a mammal comprising administering to the mammal the compound or salt according to claim 1, wherein the condition or disorder is selected from gastroesophageal reflux disorder, functional dyspepsia, irritable bowel syndrome, constipation, intestinal pseudo-obstruction, paralytic ileus following surgery, emesis, gastric stasis or hypomotility caused by diabetes and/or by the administration of other drugs, Crohn's disease, and colitis.

4. A method of treatment for a condition or disorder which is mediated via GPR-38 receptors in a mammal comprising administering to the mammal the compound or salt according to claim 1, wherein the condition or disorder is selected from gastroesophageal reflux disorder, intestinal pseudo-obstruction, paralytic ileus following surgery, emesis, and gastric stasis or hypomotility caused by diabetes and/ or by the administration of other drugs.

5. A method of treatment for gastric stasis or hypomotility caused by diabetes in a mammal comprising administering to the mammal the compound or salt according to claim 1.

6. A method of treatment for gastric stasis or hypomotility caused by the administration of other drugs in a mammal comprising administering to the mammal the compound or salt according to claim 1.

7. A method of treatment for paralytic ileus following surgery in a mammal comprising administering to the mammal the compound or salt according to claim 1.

8. A method of treatment for intestinal pseudo-obstruction in a mammal comprising administering to the mammal the compound or salt according to claim 1.

9. A compound which is N-(3-Fluorophenyl)-1-[(4-{[(3S)-3-methyl-1-piperazinyl]methyl}phenyl)acetyl]-4-piperidinamine having the formula:

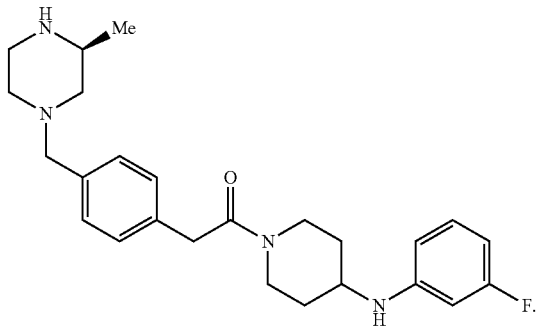 [SMILES: C[C@H]1CN(Cc2ccc(CC(=O)N3CCC(Nc4cccc(F)c4)CC3)cc2)CCN1]

10. A pharmaceutical composition comprising the compound according to claim 9.

11. A method of treatment for a condition or disorder which is mediated via GPR-38 receptors in a mammal comprising administering to the mammal the compound according to claim 9, wherein the condition or disorder is selected from gastroesophageal reflux disorder, functional dyspepsia, irritable bowel syndrome, constipation, intestinal pseudo-obstruction, paralytic ileus following surgery, emesis, gastric stasis or hypomotility caused by diabetes and/ or by the administration of other drugs, Crohn's disease, and colitis.

12. A method of treatment for a condition or disorder which is mediated via GPR-38 receptors in a mammal comprising administering to the mammal the compound according to claim 9, wherein the condition or disorder is gastroesophageal reflux disorder, intestinal pseudo-obstruction, paralytic ileus following surgery, emesis and gastric stasis or hypomotility caused by diabetes and/ or by the administration of other drugs.

13. A method of treatment for gastric stasis or hypomotility caused by diabetes in a mammal comprising administering to the mammal the compound according to claim 9.

14. A method of treatment for gastric stasis or hypomotility caused by the administration of other drugs in a mammal comprising administering to the mammal the compound according to claim 9.

15. A method of treatment for paralytic ileus following surgery in a mammal comprising administering to the mammal the compound according to claim 9.

16. A method of treatment for intestinal pseudo-obstruction in a mammal comprising administering to the mammal the compound according to claim 9.

* * * * *

UNITED STATES PATENT AND TRADEMARK OFFICE
CERTIFICATE OF CORRECTION

| | | |
|---|---|---|
| PATENT NO. | : 8,536,182 B2 | Page 1 of 1 |
| APPLICATION NO. | : 11/996650 | |
| DATED | : September 17, 2013 | |
| INVENTOR(S) | : Johnson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1078 days.

Signed and Sealed this
Twelfth Day of May, 2015

Michelle K. Lee
*Director of the United States Patent and Trademark Office*